United States Patent
Liu et al.

(10) Patent No.: US 10,610,412 B2
(45) Date of Patent: *Apr. 7, 2020

(54) TYMPANIC MEMBRANE PRESSURE EQUALIZATION TUBE DELIVERY SYSTEM

(71) Applicant: Tusker Medical, Inc., Menlo Park, CA (US)

(72) Inventors: Greg Liu, Sunnyvale, CA (US); Rohit Girotra, San Francisco, CA (US); John H. Morriss, San Francisco, CA (US); Julia D. Vrany, Los Altos, CA (US); Hung V. Ha, San Jose, CA (US); Bryan D. Knodel, Flagstaff, AZ (US); Jeffrey A. Walker, Livermore, CA (US); Thomas D. Gross, Los Gatos, CA (US); Mathew D. Clopp, Santa Clara, CA (US); Bernard H. Andreas, Redwood City, CA (US)

(73) Assignee: Tusker Medical, Inc., Menlo Park, CA (US)

( * ) Notice: Subject to any disclaimer, the term of this patent is extended or adjusted under 35 U.S.C. 154(b) by 194 days.

This patent is subject to a terminal disclaimer.

(21) Appl. No.: 15/675,093

(22) Filed: Aug. 11, 2017

(65) Prior Publication Data

US 2018/0055693 A1 Mar. 1, 2018

Related U.S. Application Data

(63) Continuation of application No. 14/570,157, filed on Dec. 15, 2014, now Pat. No. 9,770,366, which is a (Continued)

(51) Int. Cl.
  *A61F 11/00* (2006.01)
  *A61B 17/34* (2006.01)
  *A61B 17/30* (2006.01)

(52) U.S. Cl.
  CPC ........ *A61F 11/002* (2013.01); *A61B 17/3468* (2013.01); *A61B 17/3478* (2013.01); *A61B 2017/306* (2013.01)

(58) Field of Classification Search
  CPC ............... A61F 11/002; A61B 17/3478; A61B 17/3468
  See application file for complete search history.

(56) References Cited

U.S. PATENT DOCUMENTS

| 858,673 A | 7/1907 | Roswell |
| 1,920,006 A | 7/1933 | Dozier et al. |

(Continued)

FOREIGN PATENT DOCUMENTS

| CN | 86105171 A | 3/1987 |
| CN | 2635015 Y | 8/2004 |

(Continued)

OTHER PUBLICATIONS

U.S. Appl. No. 61/225,893, filed Jul. 15, 2009.
(Continued)

*Primary Examiner* — Richard G Louis

(57) ABSTRACT

Systems and methods are provided for automatically forming an incision in a tympanic membrane of an ear and placing a tympanic membrane pressure equalization tube into the incision. The systems include a housing with a shaft extending therefrom. A mechanism is disposed within the housing. A distal end of the shaft is placed against a tympanic membrane, and the mechanism is triggered to causes the tympanic membrane to be automatically incised and dilated and a tympanic membrane pressure equalization tube to be placed in the dilated incision.

16 Claims, 19 Drawing Sheets

Related U.S. Application Data continuation-in-part of application No. 14/457,412, filed on Aug. 12, 2014, now Pat. No. 9,539,146, which is a continuation-in-part of application No. 12/836,654, filed on Jul. 15, 2010, now Pat. No. 8,864,774.

(60) Provisional application No. 61/225,893, filed on Jul. 15, 2009.

(56) References Cited

U.S. PATENT DOCUMENTS

| | | |
|---|---|---|
| 2,162,681 A | 6/1939 | Ryan |
| 3,473,170 A | 10/1969 | Haase et al. |
| 3,638,643 A | 2/1972 | Hotchkiss |
| 3,741,197 A | 6/1973 | Sanz et al. |
| 3,807,404 A | 4/1974 | Weissman et al. |
| 3,888,258 A | 6/1975 | Akiyama |
| 3,897,786 A | 8/1975 | Garnett et al. |
| 3,913,584 A | 10/1975 | Walchle et al. |
| 3,948,271 A * | 4/1976 | Akiyama ............ A61F 11/002 604/540 |
| 3,991,755 A | 11/1976 | Vernon et al. |
| 4,168,697 A | 9/1979 | Cantekin |
| 4,335,713 A | 6/1982 | Komiya |
| 4,335,715 A | 6/1982 | Kirkley |
| 4,380,998 A | 4/1983 | Kieffer, III et al. |
| 4,406,282 A | 9/1983 | Parker et al. |
| 4,468,218 A | 8/1984 | Armstrong |
| 4,473,073 A | 9/1984 | Darnell |
| 4,552,137 A | 11/1985 | Strauss |
| 4,564,009 A | 1/1986 | Brinkhoff |
| 4,712,537 A | 12/1987 | Pender |
| 4,750,491 A | 6/1988 | Kaufman et al. |
| 4,796,624 A | 1/1989 | Trott et al. |
| 4,800,876 A | 1/1989 | Fox et al. |
| 4,913,132 A | 4/1990 | Gabriel |
| 4,946,440 A | 8/1990 | Hall |
| 4,964,850 A | 10/1990 | Bouton et al. |
| 4,968,296 A | 11/1990 | Ritch et al. |
| 4,971,076 A | 11/1990 | Densert et al. |
| 5,026,378 A | 6/1991 | Goldsmith, III |
| 5,044,373 A | 9/1991 | Northeved et al. |
| 5,047,007 A | 9/1991 | McNichols et al. |
| 5,053,040 A | 10/1991 | Goldsmith, III |
| 5,092,837 A | 3/1992 | Ritch et al. |
| 5,107,861 A | 4/1992 | Narboni |
| 5,135,478 A | 8/1992 | Sibalis |
| 5,158,540 A | 10/1992 | Wijay |
| 5,178,623 A | 1/1993 | Cinberg et al. |
| 5,254,120 A | 10/1993 | Cinberg et al. |
| 5,261,903 A | 11/1993 | Dhaliwal et al. |
| D352,780 S | 11/1994 | Glaeser et al. |
| 5,370,656 A | 12/1994 | Shevel |
| 5,421,818 A | 6/1995 | Arenberg |
| 5,466,239 A | 11/1995 | Cinberg et al. |
| 5,489,286 A | 2/1996 | Cinberg et al. |
| 5,496,329 A | 3/1996 | Reisinger |
| D378,611 S | 3/1997 | Croley |
| 5,610,988 A | 3/1997 | Miyahara |
| 5,643,280 A | 7/1997 | Del Rio et al. |
| 5,645,584 A | 7/1997 | Suyama |
| 5,658,235 A | 8/1997 | Priest et al. |
| 5,674,196 A | 10/1997 | Donaldson et al. |
| 5,676,635 A | 10/1997 | Levin |
| 5,681,323 A | 10/1997 | Arick |
| D387,863 S | 12/1997 | Herman et al. |
| 5,707,383 A | 1/1998 | Bays et al. |
| 5,775,336 A | 7/1998 | Morris |
| 5,782,744 A | 7/1998 | Money |
| 5,792,100 A | 8/1998 | Shantha |
| 5,810,848 A | 9/1998 | Hayhurst |
| 5,827,295 A | 10/1998 | Del Rio et al. |
| 5,893,828 A | 4/1999 | Uram |
| 5,893,837 A | 4/1999 | Eagles et al. |
| 5,984,930 A | 11/1999 | Maciunas et al. |
| D418,223 S | 12/1999 | Phipps et al. |
| D420,741 S | 2/2000 | Croley |
| 6,022,342 A | 2/2000 | Mukherjee |
| 6,024,726 A | 2/2000 | Hill |
| 6,039,748 A | 3/2000 | Savage et al. |
| 6,045,528 A | 4/2000 | Arenberg et al. |
| D424,197 S | 5/2000 | Sydlowski et al. |
| 6,059,803 A | 5/2000 | Spilman |
| D426,135 S | 6/2000 | Lee |
| 6,077,179 A | 6/2000 | Liechty, II |
| 6,110,196 A | 8/2000 | Edwards |
| 6,137,889 A | 10/2000 | Shennib et al. |
| 6,171,236 B1 | 1/2001 | Bonutti |
| 6,183,469 B1 | 2/2001 | Thapliyal et al. |
| 6,200,280 B1 | 3/2001 | Brenneman et al. |
| 6,206,888 B1 | 3/2001 | Bicek et al. |
| 6,245,077 B1 | 6/2001 | East et al. |
| 6,248,112 B1 | 6/2001 | Gambale et al. |
| 6,251,121 B1 | 6/2001 | Saadat |
| 6,258,067 B1 | 7/2001 | Hill |
| D450,843 S | 11/2001 | McGuckin, Jr. et al. |
| 6,319,199 B1 | 11/2001 | Sheehan et al. |
| 6,358,231 B1 | 3/2002 | Schncher et al. |
| 6,398,758 B1 | 6/2002 | Jacobsen et al. |
| 6,440,102 B1 | 6/2002 | Arenberg et al. |
| 6,416,512 B1 | 7/2002 | Ellman et al. |
| 6,447,522 B2 | 9/2002 | Gambale et al. |
| 6,475,138 B1 | 11/2002 | Schechter et al. |
| 6,512,950 B2 | 1/2003 | Li et al. |
| 6,514,261 B1 | 2/2003 | Randall et al. |
| 6,520,939 B2 | 2/2003 | Lafontaine |
| 6,522,897 B1 | 2/2003 | Loeb et al. |
| 6,553,253 B1 | 4/2003 | Chang |
| 6,645,173 B1 | 11/2003 | Liebowitz |
| 6,648,873 B2 | 11/2003 | Arenberg et al. |
| 6,663,575 B2 | 12/2003 | Leysieffer |
| 6,682,558 B2 | 1/2004 | Tu et al. |
| 6,770,080 B2 | 8/2004 | Kaplan et al. |
| 6,916,159 B2 | 7/2005 | Rush et al. |
| 6,962,595 B1 | 11/2005 | Chamness et al. |
| 7,127,285 B2 | 10/2006 | Henley et al. |
| 7,137,975 B2 | 11/2006 | Miller et al. |
| D535,027 S | 1/2007 | James et al. |
| 7,160,274 B2 | 1/2007 | Ciok et al. |
| 7,344,507 B2 | 3/2008 | Briggs et al. |
| 7,351,246 B2 | 4/2008 | Epley |
| 7,381,210 B2 | 6/2008 | Zarbatany et al. |
| D595,410 S | 6/2009 | Luzon |
| 7,563,232 B2 | 7/2009 | Freeman et al. |
| D598,543 S | 8/2009 | Vogel et al. |
| 7,654,997 B2 | 2/2010 | Makower et al. |
| 7,677,734 B2 | 3/2010 | Wallace |
| 7,704,259 B2 | 4/2010 | Kaplan et al. |
| 7,749,754 B2 | 7/2010 | Sobelman et al. |
| D622,842 S | 8/2010 | Benoist |
| 7,909,220 B2 | 3/2011 | Viola |
| D640,374 S | 6/2011 | Liu et al. |
| 8,052,693 B2 | 11/2011 | Shahoian |
| 8,192,420 B2 | 6/2012 | Morriss et al. |
| 8,249,700 B2 | 8/2012 | Clifford et al. |
| 8,282,648 B2 | 10/2012 | Tekulve |
| 8,409,175 B2 | 4/2013 | Lee et al. |
| 8,425,488 B2 | 4/2013 | Clifford et al. |
| 8,498,425 B2 | 7/2013 | Graylin |
| 8,518,098 B2 | 8/2013 | Roeder et al. |
| 8,702,722 B2 | 4/2014 | Shahoian |
| 8,840,602 B2 | 9/2014 | Morriss et al. |
| 8,849,394 B2 | 9/2014 | Clifford et al. |
| 8,864,774 B2 | 10/2014 | Liu et al. |
| 8,998,927 B2 | 4/2015 | Kaplan et al. |
| 9,011,363 B2 | 4/2015 | Clopp et al. |
| 9,023,059 B2 | 5/2015 | Loushin et al. |
| 9,216,112 B2 | 12/2015 | Clifford et al. |
| 9,320,652 B2 | 4/2016 | Andreas et al. |
| 9,387,124 B2 | 7/2016 | Clifford |
| 9,539,146 B2 | 1/2017 | Girotra et al. |
| 9,681,891 B2 | 6/2017 | Andreas et al. |
| 9,707,131 B2 | 7/2017 | Shahoian |

(56) References Cited

U.S. PATENT DOCUMENTS

| | | |
|---|---|---|
| 9,770,366 B2 | 9/2017 | Liu et al. |
| 9,833,359 B2 | 12/2017 | Clopp |
| 9,833,360 B2 | 12/2017 | Andreas et al. |
| 9,833,601 B2 | 12/2017 | Clifford |
| 10,130,515 B2 | 11/2018 | Kaplan et al. |
| 10,195,086 B2 | 2/2019 | Van et al. |
| 10,219,950 B2 | 3/2019 | Andreas et al. |
| 10,258,776 B2 | 4/2019 | Clifford et al. |
| 2001/0020173 A1 | 9/2001 | Klumb et al. |
| 2002/0026125 A1 | 2/2002 | Leysieffer |
| 2002/0069883 A1 | 6/2002 | Hirchenbain |
| 2002/0111585 A1 | 8/2002 | Lafontaine |
| 2002/0138091 A1 | 9/2002 | Pflueger |
| 2002/0161379 A1 | 10/2002 | Kaplan et al. |
| 2002/0169456 A1 | 11/2002 | Tu et al. |
| 2003/0018291 A1 | 1/2003 | Hill et al. |
| 2003/0040717 A1 | 2/2003 | Saulenas et al. |
| 2003/0060799 A1 | 3/2003 | Arenberg et al. |
| 2003/0097178 A1 | 5/2003 | Roberson et al. |
| 2003/0120292 A1 | 6/2003 | Park et al. |
| 2003/0187456 A1 | 10/2003 | Perry |
| 2003/0199791 A1 | 10/2003 | Boecker et al. |
| 2004/0054339 A1 | 3/2004 | Ciok et al. |
| 2004/0064024 A1 | 4/2004 | Sommer |
| 2005/0033343 A1 | 2/2005 | Chermoni |
| 2005/0070765 A1* | 3/2005 | Abdelgany ............ A61B 17/02 600/214 |
| 2005/0165388 A1 | 7/2005 | Py et al. |
| 2005/0182385 A1 | 8/2005 | Epley |
| 2005/0187546 A1 | 8/2005 | Bek et al. |
| 2005/0203552 A1 | 9/2005 | Laufer et al. |
| 2005/0235422 A1 | 10/2005 | Wallace |
| 2005/0240147 A1 | 10/2005 | Makower et al. |
| 2006/0004323 A1 | 1/2006 | Chang et al. |
| 2006/0095050 A1 | 5/2006 | Hartley et al. |
| 2006/0142700 A1 | 6/2006 | Sobelman et al. |
| 2006/0155304 A1 | 7/2006 | Kaplan et al. |
| 2006/0161218 A1 | 7/2006 | Danilov |
| 2006/0163313 A1 | 7/2006 | Larson |
| 2006/0282062 A1 | 12/2006 | Ishikawa et al. |
| 2007/0088247 A1 | 4/2007 | Bliweis et al. |
| 2007/0233222 A1 | 10/2007 | Roeder et al. |
| 2007/0276466 A1 | 11/2007 | Lavelle et al. |
| 2008/0027423 A1 | 1/2008 | Choi et al. |
| 2008/0051804 A1 | 2/2008 | Cottler et al. |
| 2008/0065011 A1 | 3/2008 | Marchand et al. |
| 2008/0083813 A1 | 4/2008 | Zemlock et al. |
| 2008/0212416 A1 | 9/2008 | Polonio et al. |
| 2008/0262468 A1 | 10/2008 | Clifford et al. |
| 2008/0262508 A1 | 10/2008 | Clifford et al. |
| 2008/0262510 A1 | 10/2008 | Clifford |
| 2009/0163828 A1 | 6/2009 | Turner et al. |
| 2009/0171271 A1 | 7/2009 | Webster et al. |
| 2009/0209972 A1 | 8/2009 | Loushin et al. |
| 2009/0299344 A1 | 12/2009 | Lee et al. |
| 2009/0299379 A1* | 12/2009 | Katz ..................... A61F 11/002 606/109 |
| 2009/0299433 A1 | 12/2009 | Lee |
| 2010/0041447 A1 | 2/2010 | Graylin |
| 2010/0048978 A1 | 2/2010 | Sing et al. |
| 2010/0061581 A1 | 3/2010 | Soetejo et al. |
| 2010/0160819 A1 | 6/2010 | Parihar et al. |
| 2010/0198135 A1 | 8/2010 | Morriss et al. |
| 2010/0217296 A1 | 8/2010 | Morriss et al. |
| 2010/0274188 A1 | 10/2010 | Chang et al. |
| 2010/0324488 A1 | 12/2010 | Smith |
| 2011/0015645 A1 | 1/2011 | Liu et al. |
| 2011/0022069 A1 | 1/2011 | Mitusina |
| 2011/0077579 A1 | 3/2011 | Harrison et al. |
| 2011/0288559 A1 | 11/2011 | Shahoian |
| 2012/0074200 A1 | 3/2012 | Schmid et al. |
| 2012/0130252 A1 | 5/2012 | Pohjanen et al. |
| 2012/0179187 A1 | 7/2012 | Loushin et al. |
| 2012/0265097 A1 | 10/2012 | Melchiorri et al. |
| 2012/0283563 A1 | 11/2012 | Moore et al. |
| 2012/0310145 A1 | 12/2012 | Clifford et al. |
| 2013/0030456 A1 | 1/2013 | Assell et al. |
| 2013/0090544 A1 | 4/2013 | Clifford et al. |
| 2013/0338678 A1 | 12/2013 | Loushin et al. |
| 2014/0094733 A1 | 4/2014 | Clopp et al. |
| 2014/0100584 A1 | 4/2014 | Konstorum et al. |
| 2014/0194891 A1 | 7/2014 | Shahoian |
| 2014/0276906 A1 | 9/2014 | Andreas et al. |
| 2014/0277050 A1 | 9/2014 | Andreas et al. |
| 2015/0142029 A1 | 5/2015 | Fahn et al. |
| 2015/0164695 A1 | 6/2015 | Liu et al. |
| 2015/0209509 A1 | 7/2015 | O'Cearbhaill et al. |
| 2015/0305944 A1 | 10/2015 | Kaplan et al. |
| 2015/0320550 A1 | 11/2015 | Downing et al. |
| 2016/0038341 A1 | 2/2016 | Clopp et al. |
| 2016/0038342 A1 | 2/2016 | Van et al. |
| 2016/0045369 A1 | 2/2016 | Clopp |
| 2016/0045370 A1 | 2/2016 | Andreas et al. |
| 2016/0045371 A1 | 2/2016 | Girotra et al. |
| 2016/0213519 A1 | 7/2016 | Andreas et al. |
| 2017/0209310 A1 | 7/2017 | Girotra et al. |
| 2017/0281230 A1 | 10/2017 | Andreas et al. |
| 2018/0085258 A1 | 3/2018 | Andreas et al. |
| 2018/0085563 A1 | 3/2018 | Clifford et al. |
| 2018/0116876 A1 | 5/2018 | Clopp |
| 2018/0303673 A1 | 10/2018 | Clopp et al. |
| 2018/0304059 A1 | 10/2018 | Clifford et al. |
| 2019/0083318 A1 | 3/2019 | Kaplan et al. |
| 2019/0201242 A1 | 7/2019 | Andreas et al. |
| 2019/0314205 A1 | 10/2019 | Van et al. |

FOREIGN PATENT DOCUMENTS

| | | |
|---|---|---|
| CN | 1933761 A | 3/2007 |
| CN | 102122067 A | 7/2011 |
| CN | 102510746 A | 6/2012 |
| CN | 102920491 A | 2/2013 |
| CN | 103327881 A | 9/2013 |
| CN | 107072690 A | 8/2017 |
| DE | 19618585 | 11/1997 |
| DE | 19918288 A1 | 10/2000 |
| EP | 0214527 A1 | 3/1987 |
| FR | 2526656 | 11/1983 |
| JP | H 07-116190 A | 5/1995 |
| JP | 2012-533359 A | 12/2012 |
| JP | 2013-523396 A | 12/2013 |
| TW | 201200098 A | 1/2012 |
| WO | WO 1999/011175 A1 | 3/1999 |
| WO | WO 1999/017825 | 4/1999 |
| WO | WO 2001/028407 | 4/2001 |
| WO | WO 2002/056756 | 7/2002 |
| WO | WO 2006/119512 | 11/2006 |
| WO | WO 2008/030485 | 3/2008 |
| WO | WO 2008/036368 | 3/2008 |
| WO | WO 2008/131195 | 10/2008 |
| WO | WO 2009/010788 | 1/2009 |
| WO | WO 2009/105619 | 8/2009 |
| WO | WO 2011/008948 | 1/2011 |
| WO | WO 2012/040430 | 3/2012 |
| WO | WO 2012/040600 | 3/2012 |
| WO | WO 2012/054934 | 4/2012 |
| WO | WO 2014/075949 | 5/2014 |
| WO | WO 2014/143543 | 9/2014 |
| WO | WO 2014/158571 | 10/2014 |
| WO | WO 2016/022899 | 2/2016 |
| WO | WO 2016/025308 | 2/2016 |
| WO | WO 2016/025309 | 2/2016 |
| WO | WO 2016/025310 | 2/2016 |
| WO | WO 2016/025453 | 2/2016 |

OTHER PUBLICATIONS

Patent Examination Report No. 1 for Australian Application No. 2010273372, dated Nov. 12, 2014, 2 pages.

Office Action for Canadian Application No. 2,768,009, dated Aug. 4, 2016, 4 pages.

First Office Action for Chinese Application No. 201080041755.6, dated Jul. 3, 2013.

(56) References Cited

OTHER PUBLICATIONS

Notification of Reasons for Refusal for Japanese Application No. 2012-520778, dated Feb. 18, 2014.
Office Action for Korean Application No. 10-2012-7003590, dated Sep. 27, 2016, 9 pages.
Communication of the Substantive Examination Report for Mexican Application No. MX/a/2012/000691, dated Apr. 24, 2014.
Office Action for U.S. Appl. No. 12/836,654, dated Sep. 28, 2012, 16 pages.
Office Action for U.S. Appl. No. 12/836,654, dated Mar. 1, 2013, 23 pages.
International Search Report for International Application No. PCT/US2010/042128, dated Aug. 27, 2010.
Written Opinion International Application No. PCT/US2010/042128, dated Aug. 27, 2010.
International Preliminary Report on Patentability for International Application No. PCT/US2010/042128, dated Jan. 17, 2012.
European Search Report for European Application No. 13173409.7, dated Sep. 16, 2013.
U.S. Appl. No. 14/457,412, filed Aug. 12, 2014.
Office Action for U.S. Appl. No. 14/457,412, dated Mar. 25, 2016, 8 pages.
International Search Report and Written Opinion for International Patent Application No. PCT/US2015/044179, dated Dec. 18, 2015, 15 pages.
Office Action for U.S. Appl. No. 14/570,157, dated Jun. 15, 2016, 6 pages.
Office Action for U.S. Appl. No. 14/570,157, dated Jan. 20, 2016, 5 pages.
Comeau, M. et al., "Local Anesthesia of the Ear by Iontophoresis," vol. 98, Arch. Otolaryngol., pp. 114-120 (Aug. 1973).
Comeau, M. et al., "Anesthesia of the Human Tympanic Membrane by Iontophoresis of a Local Anesthetic," The Larynogoscope, vol. 88, pp. 277-285 (1978).
Echols, D. F. et al., "Anesthesia of the Ear by Iontophoresis of Lidocaine," Arch. Otolaryngol., vol. 101, pp. 418-421 (Jul. 1975).
Epley, J. M., "Modified Technique of Iontophoretic Anesthesia for Myringotomy in Children," Arch. Otolaryngol., vol. 103, pp. 358-360 (Jun. 1977).
Hasegawa, M. et al., "Iontophorectic anaesthesia of the tympanic membrane," Clinical Otolaryngoloy, vol. 3, pp. 63-66 (1978).
Ramsden, R. T. et al., "Anaesthesia of the tympanic membrane using iontophoresis," The Journal of Laryngology and Otology, 56(9):779-785 (Sep. 1977).
"Definition of Plenum," Compact Oxford English Dictionary [online], Retrieved from the Internet: <http://oxforddictionaries.com/definition/english/plenum>, Retrieved on Aug. 6, 2012, 2 pages.
"Definition of Plenum," Merriam-Webster's Online Dictionary, 11th Edition [online], Retrieved from the Internet: <http://www.merriam-webster.com/dictionary/plenum>, Retrieved on Aug. 14, 2012, 1 page.

Medtronic XOMED, "Activent® Antimicrobial Ventilation Tubes," Rev. 1.1, pp. 1-4, 2002, Jacksonville, FL.
Micromedics Innovative Surgical Products, "Micromedics Tympanostomy Tubes," [online], Retrieved on Jul. 15, 2010, Retrieved from the Internet <URL: http://www.micromedics-usa.com/products/otology/micromedicstubes.htm>, 7 pages.
Armstrong, "A New Treatment for Chronic Secretory Otitis Media" A.M.A. Archives of Otolaryngology, pp. 653-654 (1954).
Feuerstein, "A Split-Tube Prosthesis in Serous Otitis Media" Sixty-ninth Annual Session of the American Academy of Ophthalmology and Otolaryngology, Oct. 18-23, 1964, Chicago, IL, pp. 343-344.
Jurgens. et al., "Three New Middle Ear Ventilation Tubes" Seventy-sixth Annual Session of the American Academy of Ophthalmology and Otolaryngology, Sep. 20-24, 1971, Las Vegas, NV, pp. 1017-1019 (1971).
Lindeman et al., the "Arrow Tube" Residents in Otolaryngology, Massachusetts Eye and Ear Infirmary, 1 page (1964).
Pappas, "Middle Ear Ventilation Tubes" Meeting of the Southern Section of the American Laryngological, Rhinological and Otological Society, Inc., Williamsburg, VA, Jan. 12, 1974, pp. 1098-1117.
Per-Lee, "A Wide Flanged Middle Ear Ventilation Tube" Seventy-first Annual Session of the American Academy of Ophthalmology and Otolaryngology, Oct. 16-21, 1966, Chicago, IL, pp. 358-359.
Reuter, "The Stainless Bobbin Middle Ear Ventilation Tube" Seventy-second Annual Session of the American Academy of Ophthalmology and Otolaryngology, Oct. 29-Nov. 3, 1967, Chicago, IL, pp. 121-122.
Ringenberg, "A New Middle Ear Ventilation Device" Seventy-second Annual Session of the American Academy of Ophthalmology and Otolaryngology, Oct. 29-Nov. 3, 1967, Chicago, IL, 1 page.
Schmidt et al. "Transtympanic Aeration of the Middle Ear With Blocked Eustachian Tube" Acta Otolaryng., pp. 277-282 (1965).
Sheehy, "Collar Button Tube for Chronic Serous Otitis" Sixty-eighth Annual Session of the American Academy of Ophthalmology and Otolaryngology, Oct. 20-25, 1963, New York, NY, pp. 888-889.
Santa Barbara Medco, Inc. "Otological Ventilation Tubes" Product Brochure from http://www.sbmedco.com/ptfe_shepard.asp, 8 pages (Feb. 11, 2001).
Rhinology Products, Boston Medical Products, www.bosmed.com, pp. 1-16, received before Jan. 2015.
Office Action for Indian Application No. 333/DELNP/2012, dated Sep. 27, 2018, 6 pages.
Extended European Search Report for European Application No. 17209149.8, dated May 7, 2018, 6 pages.
Office Action for U.S. Appl. No. 15/426,681, dated Nov. 27, 2018, 9 pages.
Office Action for Canadian Application No. 3,018,367, dated Aug. 8, 2019, 4 pages.
Office Action for U.S. Appl. No. 15/426,681, dated Aug. 21, 2019, 9 pages.

* cited by examiner

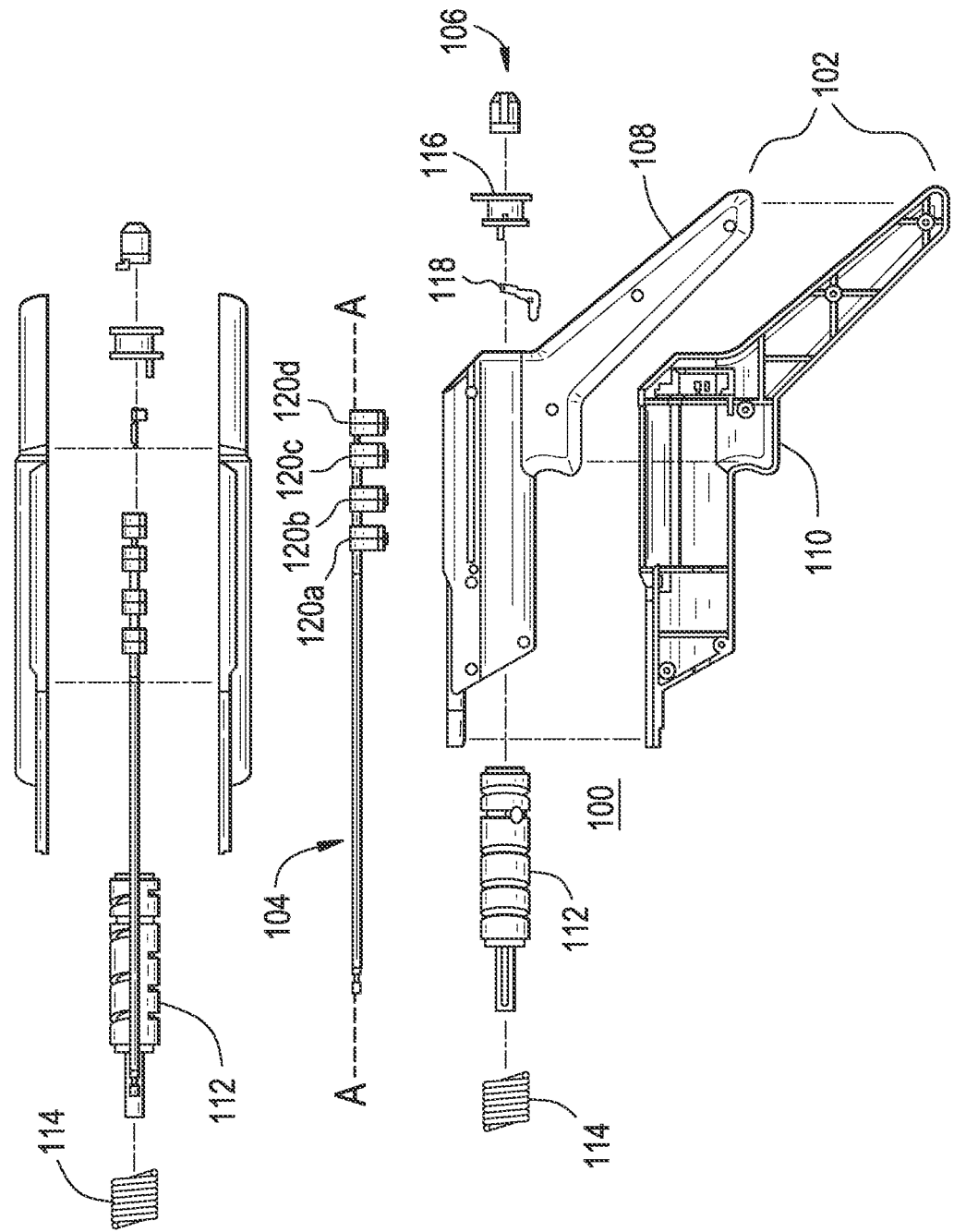

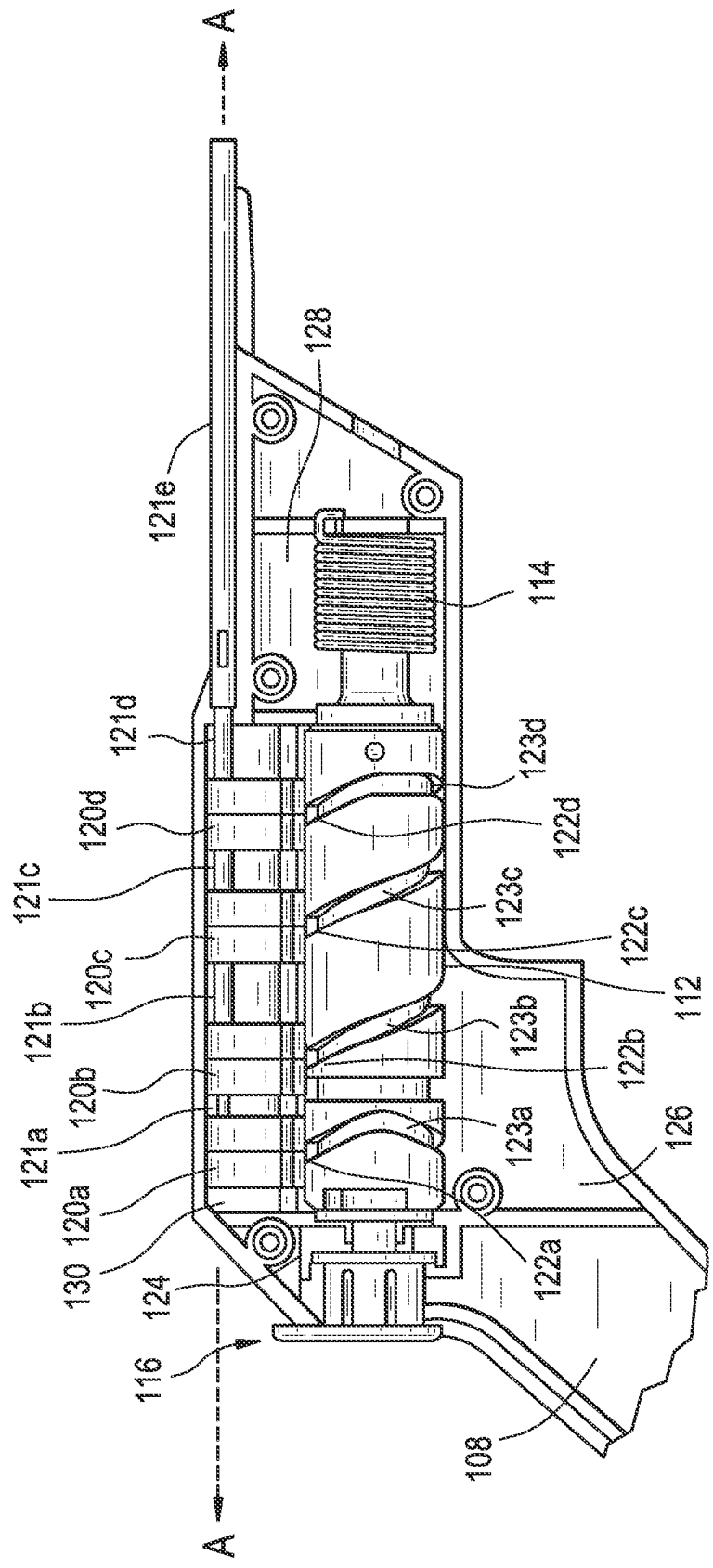

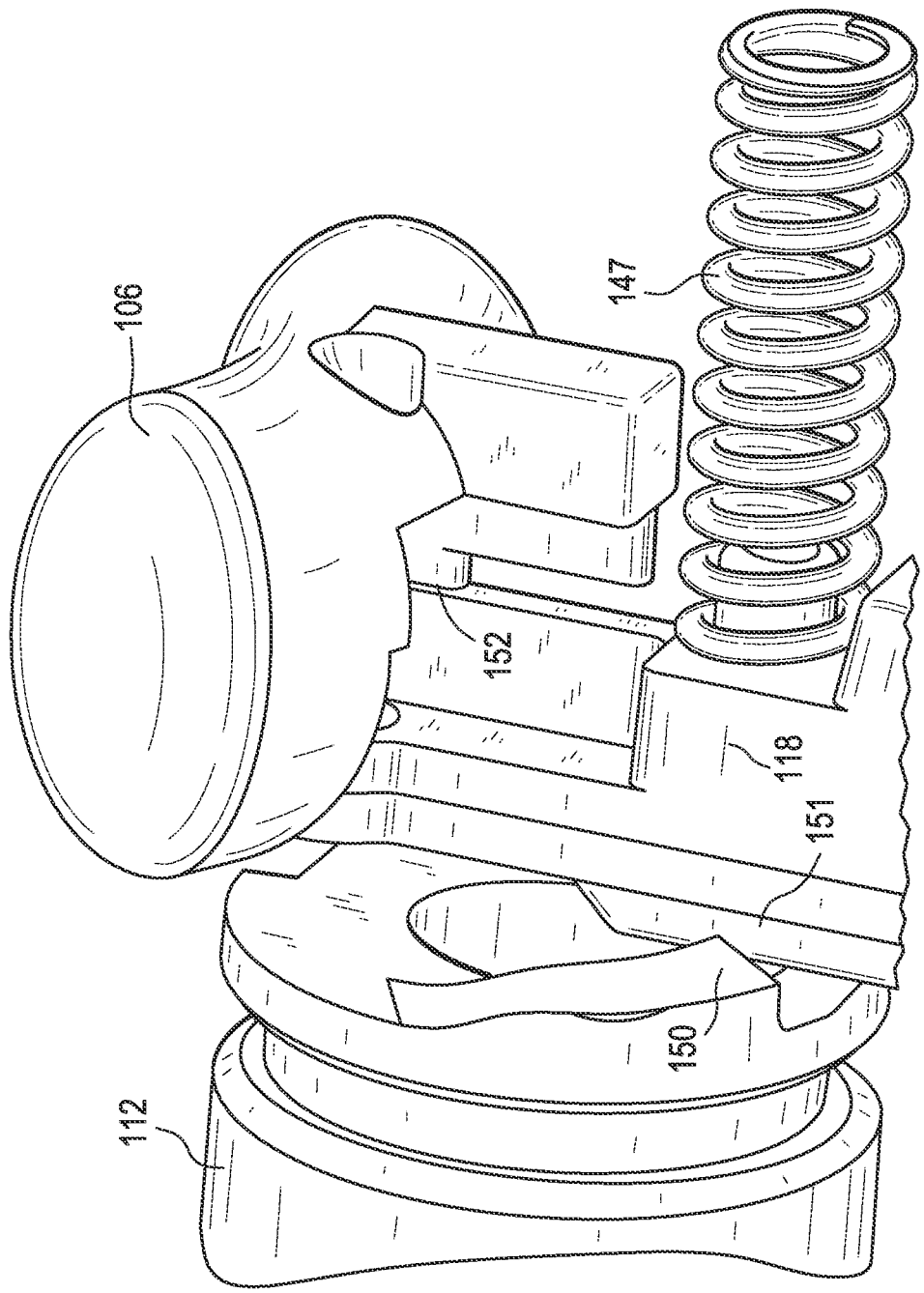

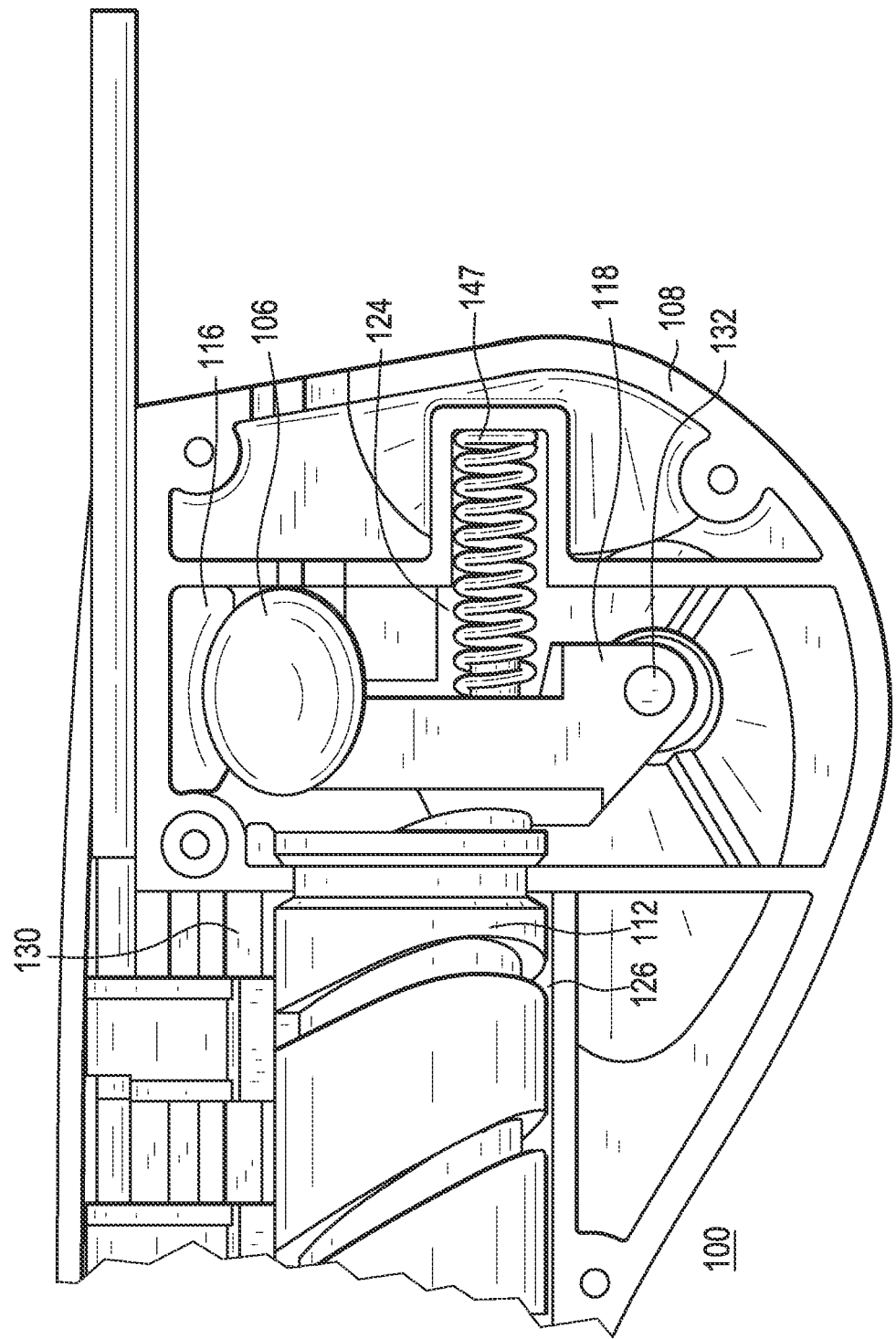

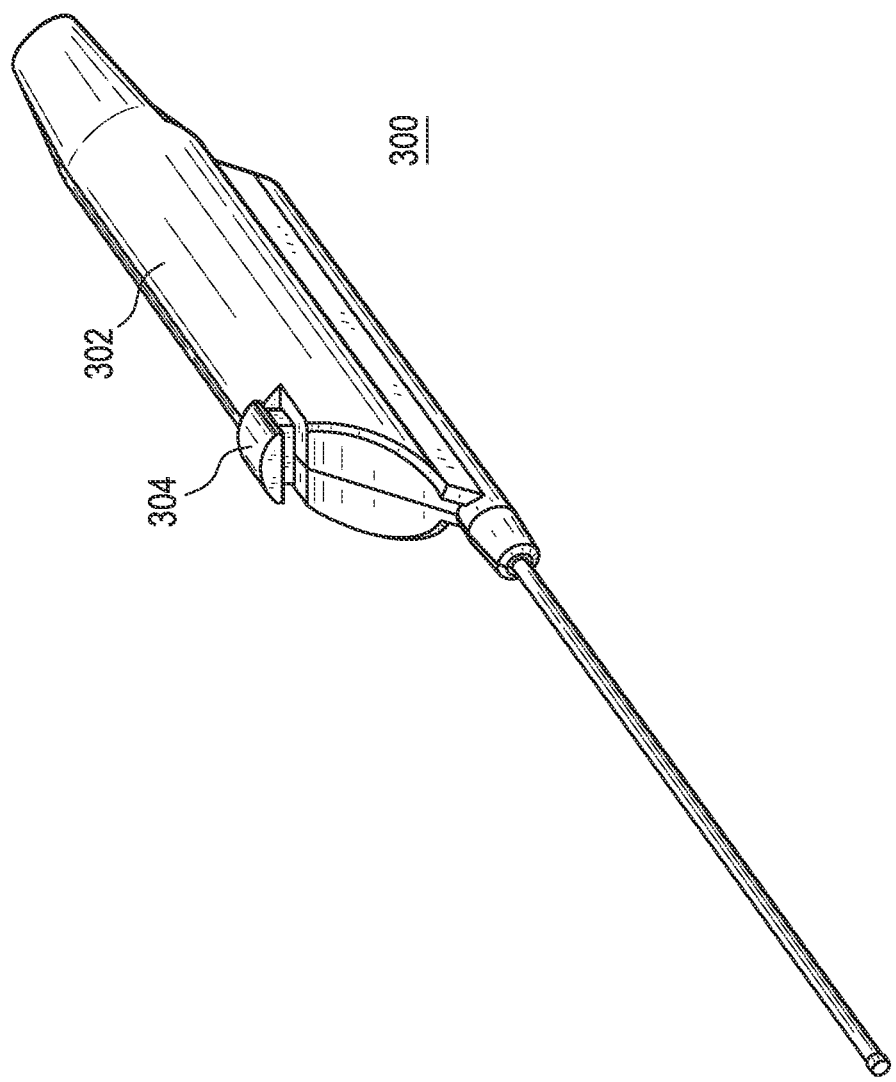

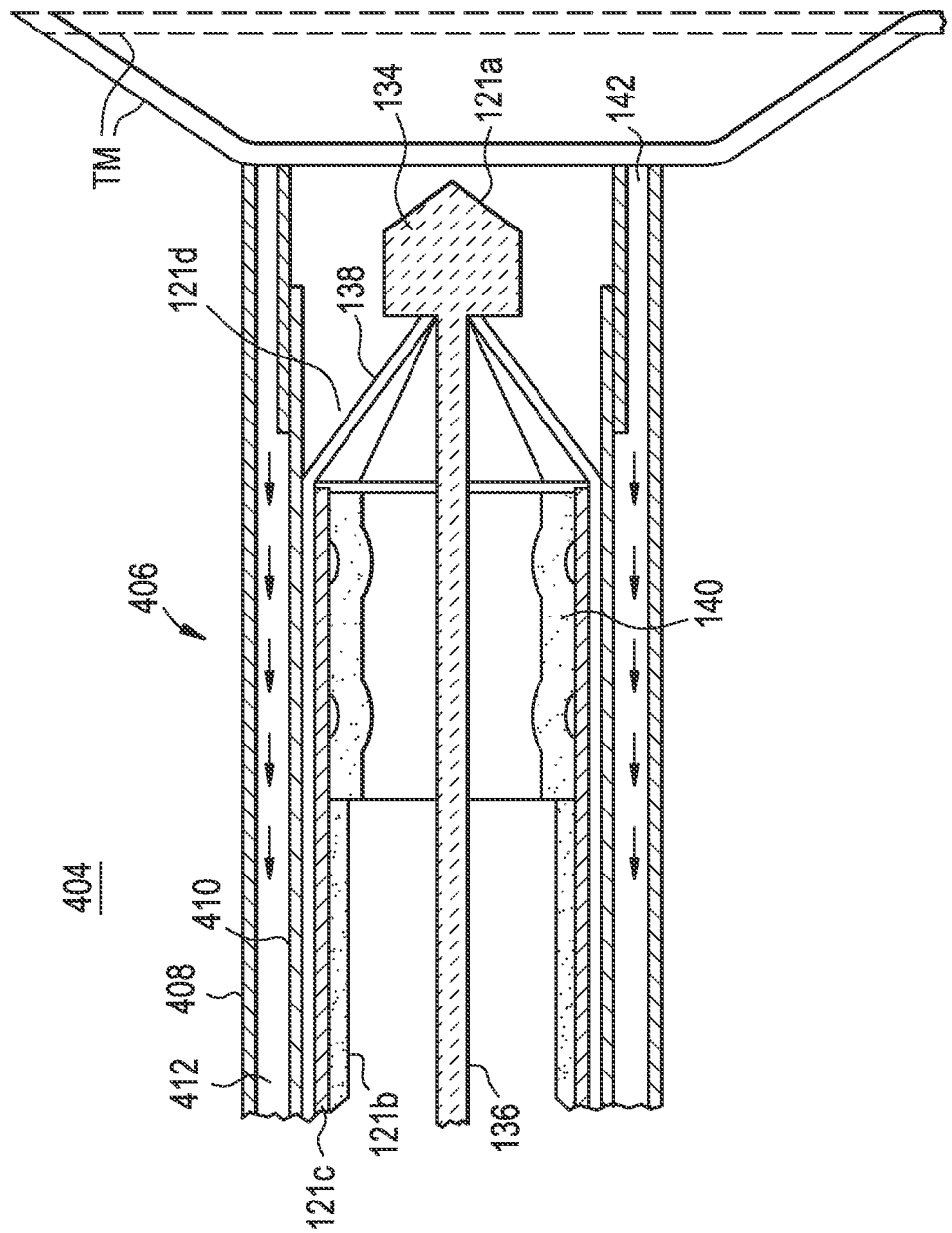

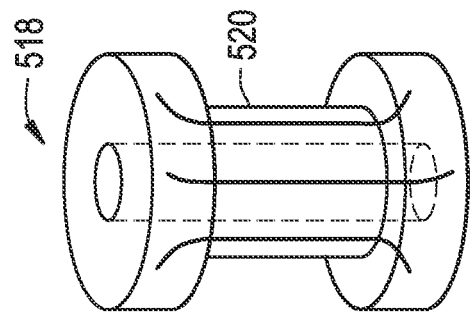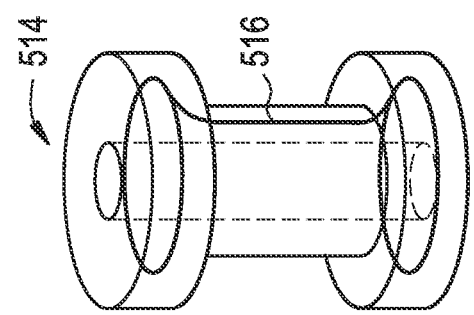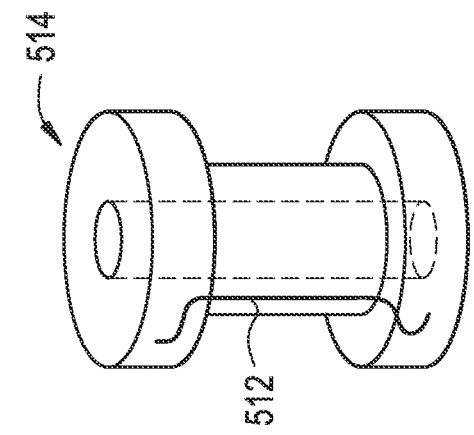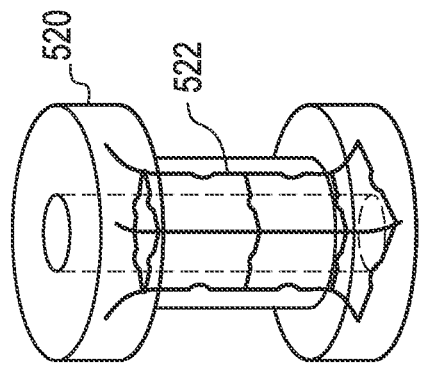

TYMPANIC MEMBRANE PRESSURE EQUALIZATION TUBE DELIVERY SYSTEM

CROSS-REFERENCE TO RELATED APPLICATIONS

This application is a continuation of U.S. patent application Ser. No. 14/570,157, entitled "TYMPANIC MEMBRANE PRESSURE EQUALIZATION TUBE DELIVERY SYSTEM," filed on Dec. 15, 2014 (now U.S. Pat. No. 9,770,366), which is a continuation-in-part of U.S. patent application Ser. No. 14/457,412, entitled "TRIGGER ASSEMBLY FOR TYMPANOSTOMY TUBE DELIVERY DEVICE," filed on Aug. 12, 2014 (now U.S. Pat. No. 9,539,146), which is a continuation-in-part of U.S. patent application Ser. No. 12/836,654, entitled "TYMPANIC MEMBRANE PRESSURE EQUALIZATION TUBE DELIVERY SYSTEM," filed on Jul. 15, 2010 (now U.S. Pat. No. 8,864,774), which claims benefit of U.S. Provisional Patent Application No. 61/225,893, entitled "TYMPANIC MEMBRANE PRESSURE EQUALIZATION TUBE DELIVERY SYSTEM," filed Jul. 15, 2009, the disclosures of each of which are herein incorporated by reference in their entireties.

BACKGROUND OF THE INVENTION

The present invention is generally related to medical devices and apparatus. In particular, the invention provides systems and methods for delivering a pressure equalization tube to a tympanic membrane of an ear.

Otitis media is among the most common diagnoses made by pediatricians. A majority of children may have at least one episode of otitis media ("earache") prior to their third birthday. Otitis media is often caused by an inability of the eustachian tube to drain fluid from the middle ear. Otitis media is often treated with antibiotics.

A significant number of children exhibit recurrent episodes of otitis media and/or otitis media with effusion. Treatment of these more severe cases often involves the placement of a tympanostomy tube through the tympanic membrane to provide adequate drainage of the middle ear and reduce the likelihood of future infections. Tympanostomy tubes provide fluid communication between the middle and outer ear (e.g., pressure equalization) and typically fall out spontaneously within about a year of placement. Tympanostomy tube placement is among the most frequent surgical procedures performed in the pediatric population. It has been estimated that more than a million tympanostomy tubes may be placed each year, with typical patients being between about 18 months and 7 years of age at the time of the procedure.

Tympanostomy tube placement is typically performed in an out-patient surgery setting under general anesthesia. The physician typically first examines the external auditory canal and tympanic membrane under microscopic visualization through a hand-held conical shaped speculum. The physician then makes an incision in the tympanic membrane (a "myringotomy"), typically using a standard, small profile scalpel which the physician advances through the conical speculum. In many cases, the physician will then place the tympanostomy tube through the tympanic membrane, typically using a basic tool for holding and advancing the tube into the myringotomy. The physician may then pass a suction device through the tube, into the middle ear, to aspirate fluid/effusion from the middle ear.

A wide variety of tympanostomy tubes is commercially available, and a still wider variety of other tubes has been proposed. Systems have also been proposed to both perform the myringotomy and deploy the tympanostomy tube with a single treatment assembly. In recent years, more complex and expensive systems have been proposed for diagnosis or treatment of the tissues of the ear, including systems using laser energy for forming a myringotomy, video systems for imaging of the ear canal, and the like. These various proposed alternatives for tympanostomy tubes and tube placement systems have met with varying degrees of acceptance. Some proposed alternatives have been overly complex, overly expensive and/or ineffective. Thus, have primarily used standard tubes and tube placement procedures and devices.

A standard tympanostomy tube placement procedure is both effective and quite safe. Nonetheless, further improvements would be desirable. For example, the standard tube placement procedure described above requires multiple tools (speculum, scalpel, tube placement device) and usually requires the patient to be under general anesthesia. Tympanostomy tube placement error can occur due to using multiple operator-performed steps and devices, and/or patient movement. The likelihood of error is increased when operating on young children under local anesthesia, as they often find it difficult to remain in a stationary position for an extended period of time.

One disadvantage of currently available tube placement methods is that the tympanostomy tubes may fall out of the tympanic membrane sooner than would be ideal. This may be due to the fact that the myringotomy must be made large enough to allow the distal flange on a standard tympanostomy tube to pass through it, and thus the typical myringotomy may be larger than ideal for holding the tube in place.

Another disadvantage of currently available tube placement methods is that the myringotomy needed to insert the tympanostomy tube is relatively large and may cause increased scaring during the healing process.

In light of the above, it would be desirable to provide improved devices, systems, and methods for delivering a pressure equalization tube to a tympanic membrane. It would generally be beneficial if these improvements facilitated tympanostomy tube placement without requiring multiple devices and operator-performed steps. At least some of these advantages may be provided by the embodiments described herein.

BRIEF SUMMARY OF THE INVENTION

The present invention provides systems and methods for automatically puncturing and delivering a tympanic membrane equalization tube (i.e., tympanostomy tube) into a tympanic membrane.

In one aspect, a system is provided for delivering a pressure equalization tube. The system includes a housing including a handle. An elongate shaft assembly is coupled with the housing. The shaft assembly includes an outer shaft having a blunt (atraumatic) distal tip portion. The distal tip portion of the elongate shaft has an inner diameter that may be equal to or larger than the inner diameter of the remainder of the outer shaft. A cutter is linearly moveable within the elongate shaft. A pusher is slidably disposed over the cutter within the elongate shaft. A pressure equalization tube is slidably disposed about the cutter at a distal end of the pusher. A shield is slidably disposed over the pusher and the pressure equalization tube. A dilator is slidably disposed over the shield. In one alternate embodiment, the cutter and the dilator may be combined as one feature as hereinafter described.

The system also includes a cam assembly. The cam assembly includes a cam shaft rotationally coupled within the housing. The cam shaft includes a first cam profile, second cam profile, a third cam profile, and a fourth cam profile. A first cam follower is moveably coupled to the first cam profile. The first cam follower is attached to the cutter. A second cam follower is moveably coupled to the second cam profile. The second cam follower is attached to the pusher. A third cam follower is moveably coupled to the third cam profile. The third cam follower is attached to the shield. A fourth cam follower is moveably coupled to the fourth cam profile. The fourth cam follower is attached to the dilator.

In one embodiment, a spring may be biased between the housing and the cam shaft. The spring has a wound position, which places torsion on the cam shaft, and a released position.

A release button may be moveably coupled to the cam shaft. The release button has a first position, which maintains the spring in the wound position, and a second position, which allows the spring to move into the released position. When the release button is moved into the released position, the spring is released to move the cam shaft and cause the cam followers to linearly move respective portions of the shaft assembly to form an incision in a tympanic membrane using the cutting member, dilate the incision using the dilator, and advance the pressure equalization tube out of the shield and into the incision using the pusher.

In another aspect, a method is provided for forming an incision and placing a pressure equalization tube in a tympanic membrane of an ear. The method includes contacting a blunt (atraumatic) distal end of a shaft of a tube delivery device with a tympanic membrane. A cutter is advanced out of the shaft distal end to form an incision in the tympanic membrane. A dilator is disposed over at least a portion of the cutter. A shield disposed over the cutter and within the dilator is advanced out of the shaft distal end and into the incision to dilate the dilator. The shield is disposed over a pressure equalization tube. The cutter is retracted into the shaft. The shield is retracted into the shaft, thereby releasing a distal flange of the pressure equalization tube such that it assumes an expanded configuration. The pressure equalization tube is pushed out of the shield using a pusher disposed within the shield, thereby releasing a proximal flange of the pressure equalization tube such that it assumes an expanded configuration. After being pushed out of the shield, a middle portion of the pressure equalization tube is disposed within the incision in the tympanic membrane and the distal and proximal flanges are disposed on opposite sides of the incision.

Advantageously, such systems and methods facilitate automatic delivery of a tympanic membrane equalization tube with minimal steps to be performed by an operator, such as advancing the system into an ear canal and triggering a release button.

For a further understanding of the nature and advantages of the invention, reference should be made to the following description taken in conjunction with the accompanying figures. However, each of the figures is provided for the purpose of illustration and description only and is not intended to limit the scope of the embodiments of the present invention.

BRIEF DESCRIPTION OF THE DRAWINGS

FIG. 3 is perspective view of a delivery system for delivering a tympanic membrane equalization tube into a tympanic membrane, according to one embodiment of the invention.

FIG. 4E is a cross-sectional view of a distal tip of a delivery system in use, according to one embodiment of the invention.

FIGS. 5D through 5G are perspective views of tympanic membrane equalization tubes, according to multiple embodiments of the invention.

DETAILED DESCRIPTION OF THE INVENTION

The embodiments of the invention are intended to provide systems for automatically puncturing and delivering a tympanic membrane equalization tube into a tympanic membrane. According to embodiments of the invention, tympanic membrane equalization tube delivery systems generally include a housing with a dedicated handgrip, or a graspable housing. A shaft extends out of the housing to access the tympanic membrane, and a tympanic membrane equalization tube is loaded within the tip of the shaft. An internal spring loaded cam-based mechanism is located within the housing and coupled to a button. The mechanism can be triggered to initiate a fast and automatic process which punctures the tympanic membrane, and delivers the tympanic membrane equalization tube. The tympanic membrane equalization tube is a grommet like device which is folded and/or compressed within the tube, and recovers its shape when delivered into the tympanic membrane.

In use, an operator grasps the housing by the handgrip and brings the tip of the shaft into contact with the tympanic membrane. The operator then triggers the cam-based mechanism by pressing the button. The system then automatically punctures and inserts the tympanic membrane equalization tube into the tympanic membrane. Thus, a simple and effective delivery system is provided, which requires minimal operator steps for use.

Embodiments of the invention are compatible for use with a suite of medical devices for visualizing, guiding other medical devices, delivering a tympanic membrane equalization tube, puncturing the tympanic membrane, and anesthetizing the tympanic membrane. Examples of such medical devices are shown in co-assigned U.S. patent application Ser. No. 11/749,733, the entirety of which is incorporated by reference. Accordingly, aspects of U.S. patent application Ser. No. 11/749,733 may be integrated, combined, and used in conjunction with the embodiments disclosed herein.

Exemplary Configurations of the Delivery System:

Two exemplary systems are described below and shown in separate figures (FIGS. 1A through 1G). Where possible, the same numbering scheme is used to identify each system's components. Clarification is added when the components of the systems vary in function.

Figure 1A:
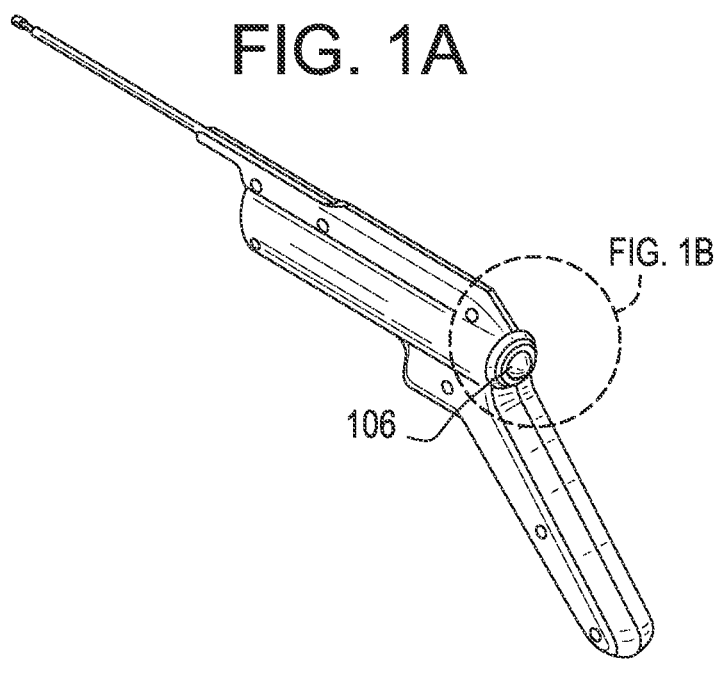
FIGS. 1A through 1G are views of delivery systems for delivering a tympanic membrane equalization tube into a tympanic membrane, according to two embodiments of the invention.
Figure 1B:
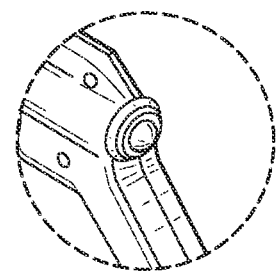
Figure 1C:
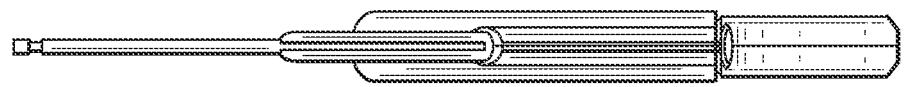
Figure 1D:
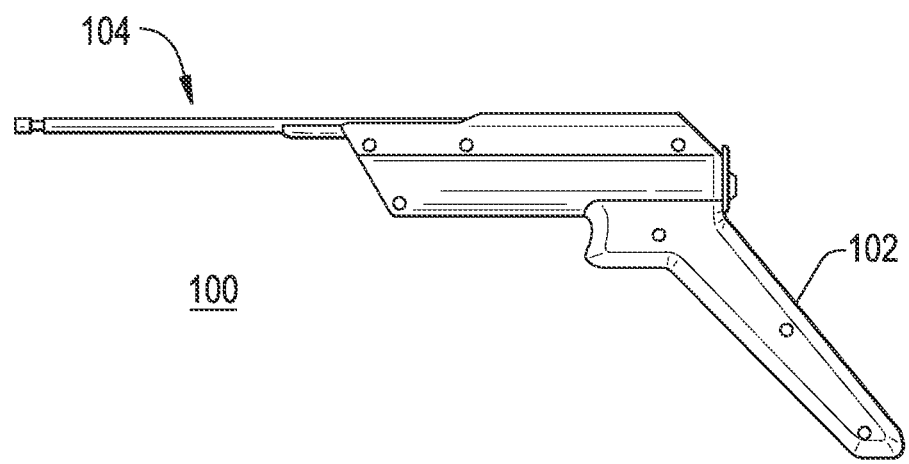
Figure 1E:
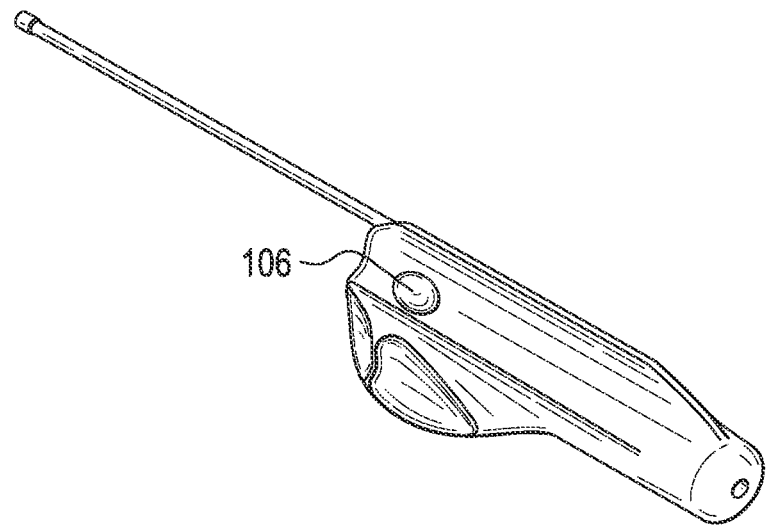
Figure 1F:
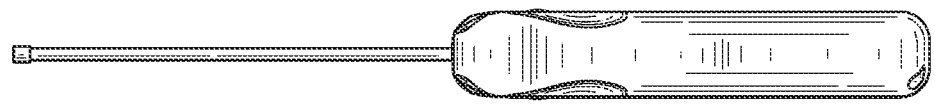
Figure 1G:
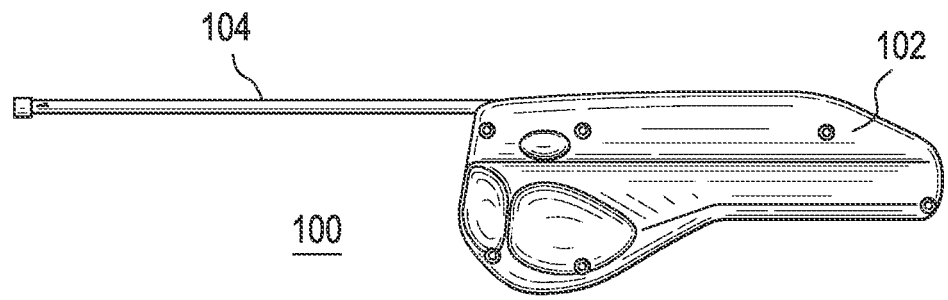

The system represented by FIGS. 1E through 1G have several advantages over the system represented by FIGS. 1A through 1D. The housing design provides a more stable and ergonomic grip enhancing device stability during usage. The spring 114 is moved to the proximal end of the delivery system 100, which aids in the more balanced and stable delivery of the tympanic membrane equalization tube.

FIGS. 1A through 1G shows a delivery system 100 for delivering a tympanic membrane equalization tube into a tympanic membrane, according to one embodiment of the invention. The delivery system 100 includes a housing 102 with a handle, or a provision for a handhold such as depicted in the overall design depicted in FIGS. 1E through 1G. A shaft assembly 104 is attached to the housing 102. The shaft assembly 104 is constructed from one or more elongate tubes, and is configured to have an outer diameter which is small enough (e.g., 2 mm) to navigate a distal portion of the shaft assembly into a tortuous path of an ear canal without requiring significant deformation of the ear canal or shaft assembly 104. In many embodiments, the shaft assembly has a preformed curvature to facilitate access to the tympanic membrane. In some embodiments the shaft assembly may be made of a malleable material(s), adjustable by the user to aid in navigating the ear canal. A tympanic membrane equalization tube (not shown) is preferably housed within the distal portion of the shaft assembly 104. A release button 106 protrudes through housing 102. The release button 106 is configured to release an internal mechanism which causes the shaft assembly 104 to automatically puncture a tympanic membrane and also insert the tympanic membrane equalization tube into the punctured tympanic membrane. In use, the delivery system 100 is used to bring the distal portion of the shaft assembly into contact, or near contact, with a tympanic membrane of an ear of a patient. The release button 106 is then manipulated to release an internal mechanism which causes the shaft assembly to automatically and swiftly puncture the tympanic membrane, and also swiftly deliver the tympanic membrane equalization tube into the punctured tympanic membrane.

FIG. 1H/1I shows a partially exploded view of the delivery system 100. The housing 102 is made up of a first housing portion 108 and a second housing portion 110, which mate together in a clamshell manner. A camshaft 112 is rotatably housed between the first housing portion 108 and a second housing portion 110. The camshaft 112 is also coupled to a spring 114, which may be biased (i.e., wound) between the housing 102 and camshaft 112. The shaft assembly 104 is movably attached to four cam followers, 120a, 120b, 120c, and 120d, each of which are slidably housed within the housing 102 along an axis A-A of the shaft assembly 104. The cam followers 120a-d are configured as slidable blocks. The release button 106 is slidably moveable within a button housing 116, which is mounted or otherwise incorporated within the housing 102. A link 118 is moveably connected between a portion of the camshaft 112 and the release button 106. The release button 106 can move or release the link 118 to disengage from the camshaft 112, and allow the spring 114 to at least partially unwind and rotate the camshaft 112, which in turn moves the cam followers 120a-d, which in turn moves portions of the shaft assembly 104 to automatically puncture the tympanic membrane, and also deliver the tympanic membrane equalization tube into the punctured tympanic membrane. Many embodiments can use other triggering mechanisms, for example, one or more fusable links may be activated by the button 106. A fusable link can be activated to erode and disengage from the camshaft 112. In some embodiments a counter balance spring 147 can be utilized to offset the loads transmitted from the spring 114 through the camshaft 112 and link 118 to the release button 106. This allows the release button 106 to move or release the link 118 with minimal force. Other embodiments may also include a lock tab 148 that holds the release button in place during handling and helps avoid unintended actuation of the device.

FIG. 1J/1K shows a portion of the delivery system 100 with the second housing portion 110 removed. The first cam follower 120a is connected to a proximal portion of a cutting member 121a. The cutting member 121a is an elongate wire or tube with a provision for puncturing (e.g. a sharpened tip) a tympanic membrane at its distal end. The second cam follower 120b is directly adjacent to the first cam follower 120a. The second cam follower 120b is connected to a proximal portion of a pusher 121b. The pusher 121b is an elongate tube within which the cutting member 121a slidably resides. The third cam follower 120c is connected to a proximal portion of a shield 121c. The shield 121c is an elongate tube within which the pusher 121b slidably resides. The fourth cam follower 120d is connected to a proximal portion of dilator 121d. The dilator 121d is an elongate tube with a distal tip capable of expanding from a narrow position to an expanded position. The shield 121c slidably resides within the dilator 121d. An outer shaft 121e is attached to the first housing portion 108. The outer shaft 121e is an elongate tube with a distal opening, and can be constructed from a stiff material, such as stainless steel.

The four cam followers 120a-d include pins 122a-d and are housed in cam follower chamber 130. Each pin 122a-d is slidable within a track 123a-d. The tracks 123a-d are profiled grooves in the circumference of the camshaft 112. As each pin 122a-d is attached to a corresponding cam follower 120a-d, movement of a pin 122a-d moves the corresponding cam follower 120a-d and a respective portion of the shaft assembly 104. For example, when the camshaft 112 is rotated, pin 122a follows track 123a, and is moved parallel to axis A-A to translate rotational movement of the camshaft 112 into linear motion of the cutting member 121a along axis A-A. Similarly, track 123b corresponds with pusher 121b; track 123c corresponds with shield 121c; and track 123d corresponds with dilator 121d.

A trigger mechanism chamber 124 houses the button housing 116. The trigger mechanism chamber 124 includes an opening for the button 106 to pass through. The first housing portion 108 is shown holding the camshaft 112 within a camshaft chamber 126, which includes rotational mounting points for the camshaft 112. A portion of the camshaft 112 extends into a spring chamber 128, where the spring 114 mounts to the camshaft 112. The spring 114 can be wound so as to be biased between the camshaft 112 and a portion of the spring chamber 128. The cam followers 120a-d are linearly arranged within a follower chamber 128.

Figure 1I:
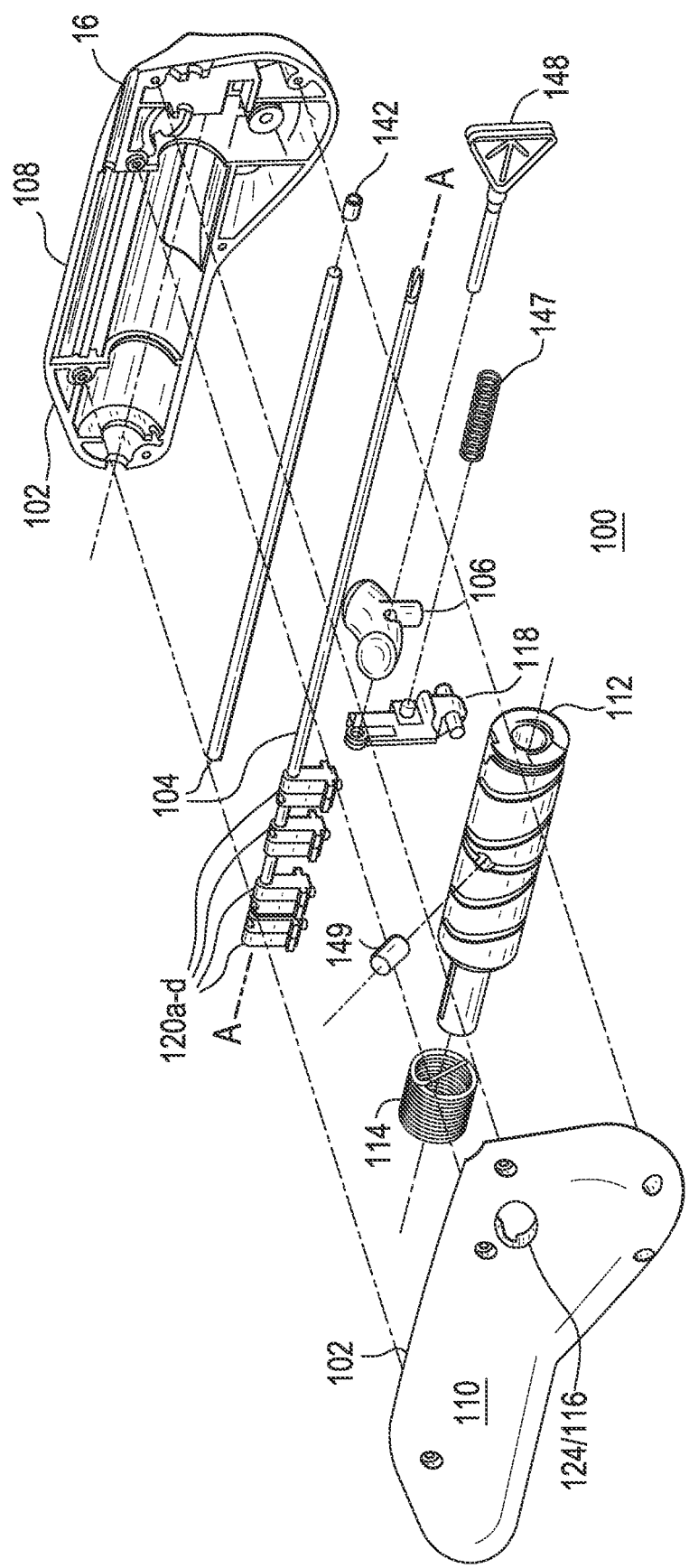
FIGS. 1H and 1I are exploded views of the delivery systems of FIGS. 1A through 1D and FIG. 1E though 1G respectively.
Figure 1K:
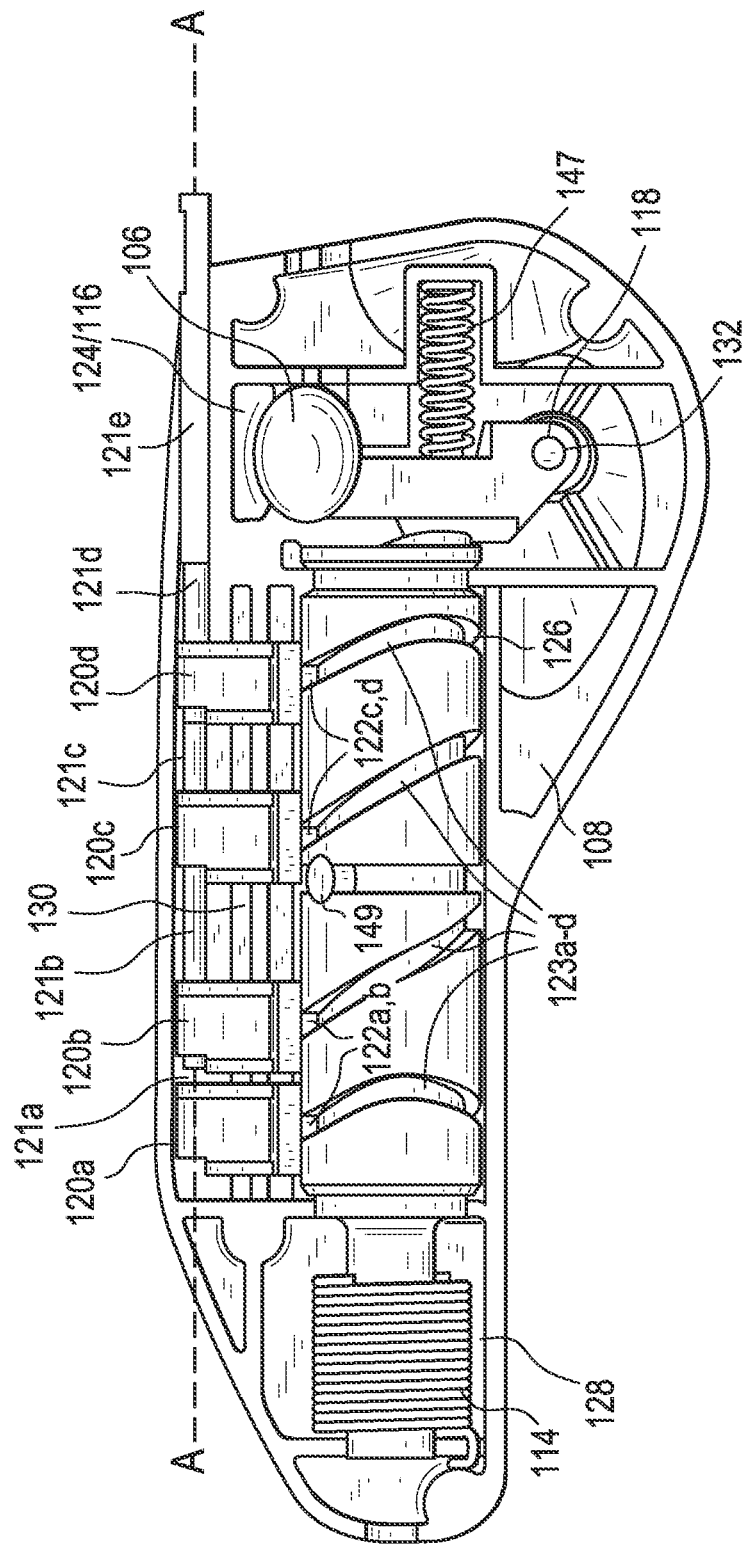
FIGS. 1J/1K and 1N/1O are a partial side views of internal portions of the delivery systems of FIG. 1A though 1D and FIGS. 1E through 1G, respectively.
FIGS. 1L and 1M are views of internal portions of the cam/switch interface of the delivery system depicted in FIGS. 1E through 1G.
FIG. 1P is a cross-sectional view of the distal tip of the delivery systems of FIGS. 1A through 1G.
Figure 1L:
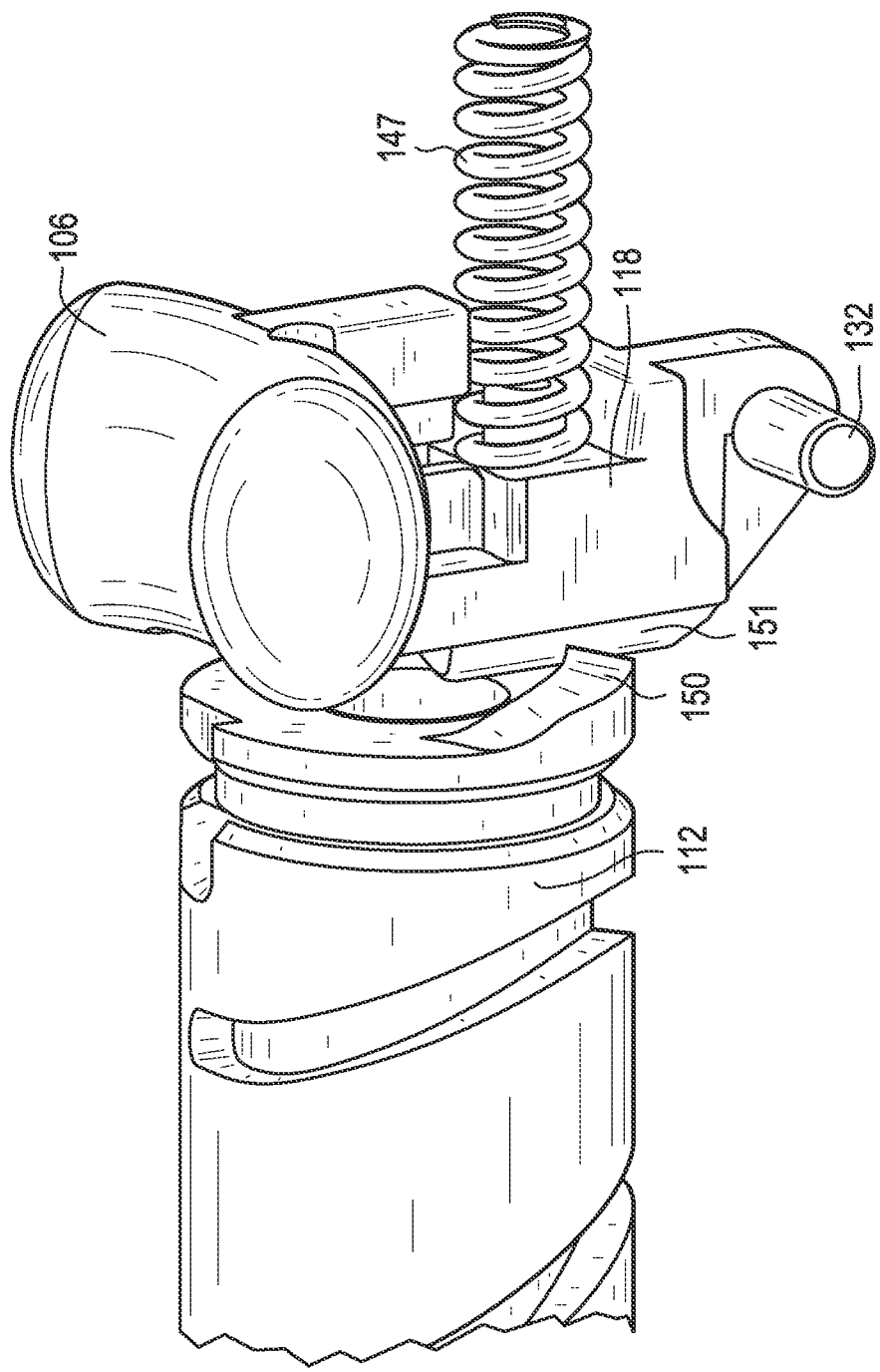

FIGS. 1L and 1M show further detail of an improved trigger mechanism that provides more consistent actuation motion and force.

FIG. 1L shows a camshaft tooth 150 extending from an end of the camshaft 112. A link tooth 151 extending from the link 118 inhibits rotational motion of the camshaft 112 when the link 118 is held in place by the release button 106.

FIG. 1M shows a perspective view of the interface 152 between the release button 106 and the link 118. Lateral movement of the release button 106 disengages the interface 152 between the release button 106 and link 118 allowing the link 118 to pivot about the link pin 132 (shown in FIG. 1L) allowing the spring 114 to at least partially unwind and rotate the camshaft 112. As described above, the counter balance spring 147 can be utilized to offset the loads transmitted from the spring 114 through the camshaft 112 and link 118 to the release button 106. This allows the release button 106 to move or release the link 118 with minimal force.

Figure 1N:
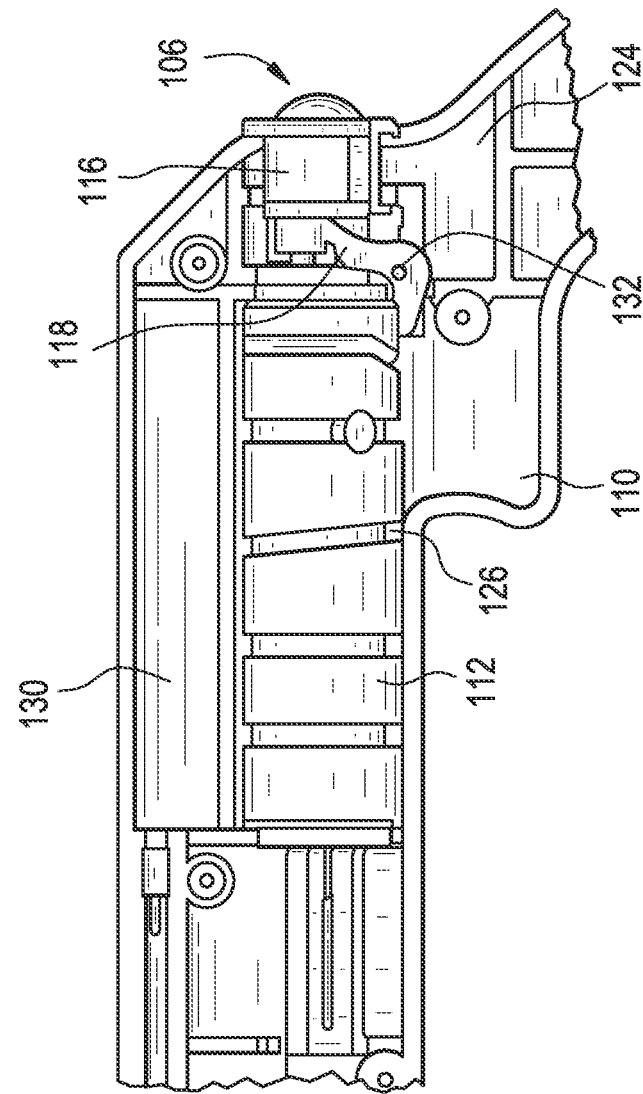

FIG. 1N/1O shows a portion of the delivery system 100 with the first housing portion 108/110 removed. The interior of the second housing portion 110 is substantially similar to the first housing portion 108 and includes internal members to form the trigger mechanism chamber 124, camshaft chamber 126, spring chamber 128 (not shown), and follower chamber 130, when mated to the first housing portion 108. The link 118 is joined to second housing portion 110/108 by a link pin 132. The link 118 pivots between the release button 106 and a portion of the camshaft 112 about the link pin 132. The spring 114 (not shown) can be wound so as to be biased between the camshaft 112 and a portion of the spring chamber 128 and kept in the biased position by the link 118. The button 106 can be pressed to decouple the link 118 from the camshaft 112, which in turn causes the wound spring 114 to unwind and rotate the camshaft 112. The camshaft 112 will rotate until it encounters a physical stop in the first or second housing portion 108, 110. The button 106 can be coupled to a safety mechanism (not shown), such as a slidable pin, button cover or lock tab which must be switched from an on position to an off position, or removed, in order to allow the button 106 to be pushed.

In many embodiments, the delivery system 100 includes provisions for noise dampening to reduce shock to the patient. After the spring 114 is released, the camshaft 112 will rotate until it encounters a stop in the first or second housing portion 108, 110, which can result in an unwanted noise which can shock the patient. The camshaft 112 and spring 114 can include lubrication and noise dampening members, such as a rubber stop 149 (such as shown in FIG. 1I and FIG. 1K, for example). The first or second housing portion can also use a non-concentric surface, instead of a sudden stop, which gradually brakes the camshaft 112. Sound baffling in the housing 102 can also be used to muffle and/or direct sound away from the ear. Sound tuning at a selected frequency and amplitude can also be employed directly prior to using the delivery system 100 to reduce shock to the patient. Introducing a noise using sound tuning causes muscles connected to the stapes to contract and reduce noise transmission to the inner ear. Sound tuning can also include generating a noise that is gradually introduced to the patient to acclimate the patient to the noise created by the delivery system 100, thus, reducing shock.

Figure 1P:
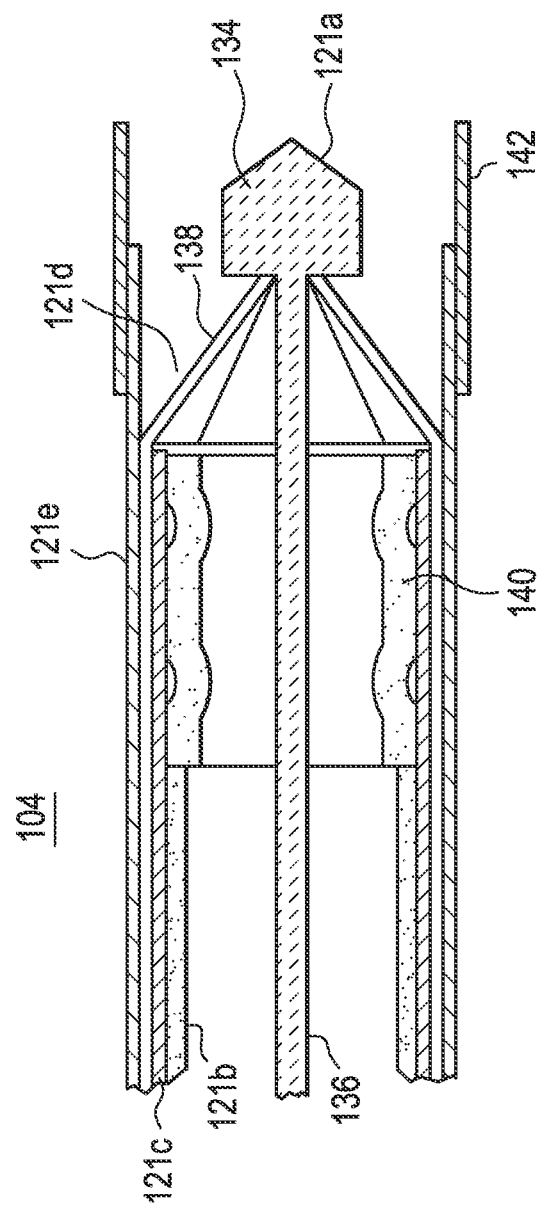

FIG. 1P shows a cross-sectional view of the distal end of the shaft assembly 104. The cutting member 121a is a diamond shaped cutting head 134 connected to an elongate wire 136. Preferably, the diamond shaped cutting head 134 is configured with multiple facets leading to a single sharp point, which can easily puncture a tympanic membrane using minimal axial force. The cutting member 121a is not limited to use of the diamond shaped cutting head 134. In many embodiments, the cutting member 121a employs a knife edged tip or a coring/non-coring needle. The cutting member 121A may also employ a wedge or planar shape with beveled edge, which may allow access to more sites of the tympanic membrane. Generally, the cutting member 121a can utilize any properly sized cutting head 134. In some embodiments, the shape of cutting head 134 may facilitate performing a myringotomy (i.e., incising a TM) without forming flaps in the TM.

The dilator 121d has a folding tip 138 which is capable of expanding from a narrow position to an expanded position. The folding tip 138 has a cone like shape when in the narrow position, as shown. The folding tip 138 abuts the back of the diamond shaped cutting head 134 when in the narrow position. The folding tip 138 can be formed by making a plurality of triangular cuts at the distal end of a tube to form folding members, and folding the folding members into a cone. The folding tip 138 generally only requires two folding members, while in this embodiment four folding members are used.

The shield 121c is a tube which is placed within the dilator 121d and proximally to the folding tip 138. When the shield 121c is moved in a distal direction, it can force open the folding tip 138. A straightened tympanic membrane equalization tube 140 is placed within the shield 121c. The tympanic membrane equalization tube 140 is restrained within the shield 121c, and proximal and distal flanges of the tube 140, which are forced into a straightened configuration within the shield 121c, apply a constant expansive force to the interior diameter of the shield 121c to stay in place. The tympanic membrane equalization tube 140 can have an interior diameter greater than the outer diameter of the diamond shaped cutting head 134 to allow removal of the tympanic membrane equalization tube 140. The tympanic membrane equalization tube 140 can also have an interior diameter equal to or smaller than the outer diameter of the diamond shaped cutting head 134, as the tympanic membrane equalization tube 140 may comprise an elastic material which allows for slight deformation/stretching of the tympanic membrane equalization tube 140 during movement of the diamond shaped cutting head 134. The pusher 121b is a tube which is placed proximally to the folded tympanic membrane equalization tube 140. The pusher 121b can be moved distally to push the folded tympanic membrane equalization tube 140 out of the shield 121c.

The outer shaft 121e surrounds the dilator 121d and is stationary with respect the movement of the other portions of the shaft assembly 104. The outer shaft 121e provides axial stiffness to the shaft assembly 104, and can be formed from a metal such as stainless steel. A tip 142 is attached to the distal end of the outer shaft 121e. The tip can be composed of a clear material to allow visualization of the tube 140 as well as anatomical structures abutting the delivery system 100 in order to facilitate accurate placement of the tube 140. Alternatively, the tip 142 may be formed from the same piece of material as the outer shaft 121e. The tip 142 includes an inner diameter which is greater than the inner diameter of the outer shaft. This larger inner diameter of the tip 142 allows a proximal flange of the tympanic membrane equalization tube 140 to open into its expanded/unconstrained configuration within the tip 142 when advanced by the pusher 121b. This expansion of the proximal flange within the tip 142 may help prevent advancement of the entire equalization tube 140 through a myringotomy into the middle ear.

In some embodiments, a pressure/contact/distance sensor may be coupled to the tip 142. The sensor provides a signal when the tip 142 contacts or is near the tympanic membrane. The signal may trigger a visual indicator (e.g., an LED) on the housing 102 to indicate that the tip 142 is in a proper position for inserting the tympanic membrane equalization tube 140 into the tympanic membrane. The sensor can be a piezoelectric, optical, capacitive based sensor, or any other suitable sensor. The signal may also trigger other operations, such triggering movement of the camshaft 112, or a sound tuning operation as described herein.

In some embodiments, the distal portion of the shaft assembly 104 may be configured to better access the tympanic membrane. The tympanic membrane has a conical shape and is angled with respect to the axis of the ear canal. Accordingly, the distal end of the shaft assembly 104 may contact the tympanic membrane at non-optimal angle (e.g. non-perpendicular). In this case, the operator may mistakenly stop short of applying sufficient pressure to the tympanic membrane to ensure complete delivery of the pressure equalization (PE) tube. In other cases, the operator may overcompensate and place too much pressure on the tympanic membrane, thus, driving the tip of the shaft assembly 104 through the tympanic membrane. To overcome these situations, the distal portion of the shaft assembly 104 can incorporate an angle such that the distal tip of the shaft assembly 104 can have better access to the tympanic membrane. In use, the operator can either rotate all or a portion of the system 100 to place the distal tip of the shaft assembly 104 in an optimal position with respect to the tympanic membrane. In some embodiments, the shaft assembly 104 is malleable so that the operator can bend the shaft assembly 104 to a desired position.

In some embodiments, the outer shaft 121e of the shaft assembly 104 includes a flexible zone, such that when the distal tip of the shaft assembly 104 presses against the tympanic membrane, the distal tip of the shaft assembly 104 automatically adjusts to an optimal position. For example, a portion of the outer shaft 121e can utilize a spring section, accordion section, or stent-like scaffold which elastically or plastically compresses when the distal tip of the shaft assembly 104 presses against the tympanic membrane. Compression of the tip can give the operator visual feedback as to the amount of pressure being applied to the tympanic membrane. In some embodiments, the outer shaft 121e has a laser cut portion removed such that a helical section exists between a mid-portion of the outer shaft 121e and a distal end of the outer shaft 121e. The helical section can be configured to flex only when sufficient pressure has been applied, thus, the operator would need to apply enough pressure to completely compress at least one side of the helical section to ensure a proper tympanic membrane equalization tube 140 delivery. In some embodiments, all or discrete portions of the shaft assembly 104 can include similar flexible zones and/or be constructed from flexible materials, for example, the cutting member 121a may be constructed from a super-elastic material (e.g., nickel-titanium alloy).

Figure 2A:
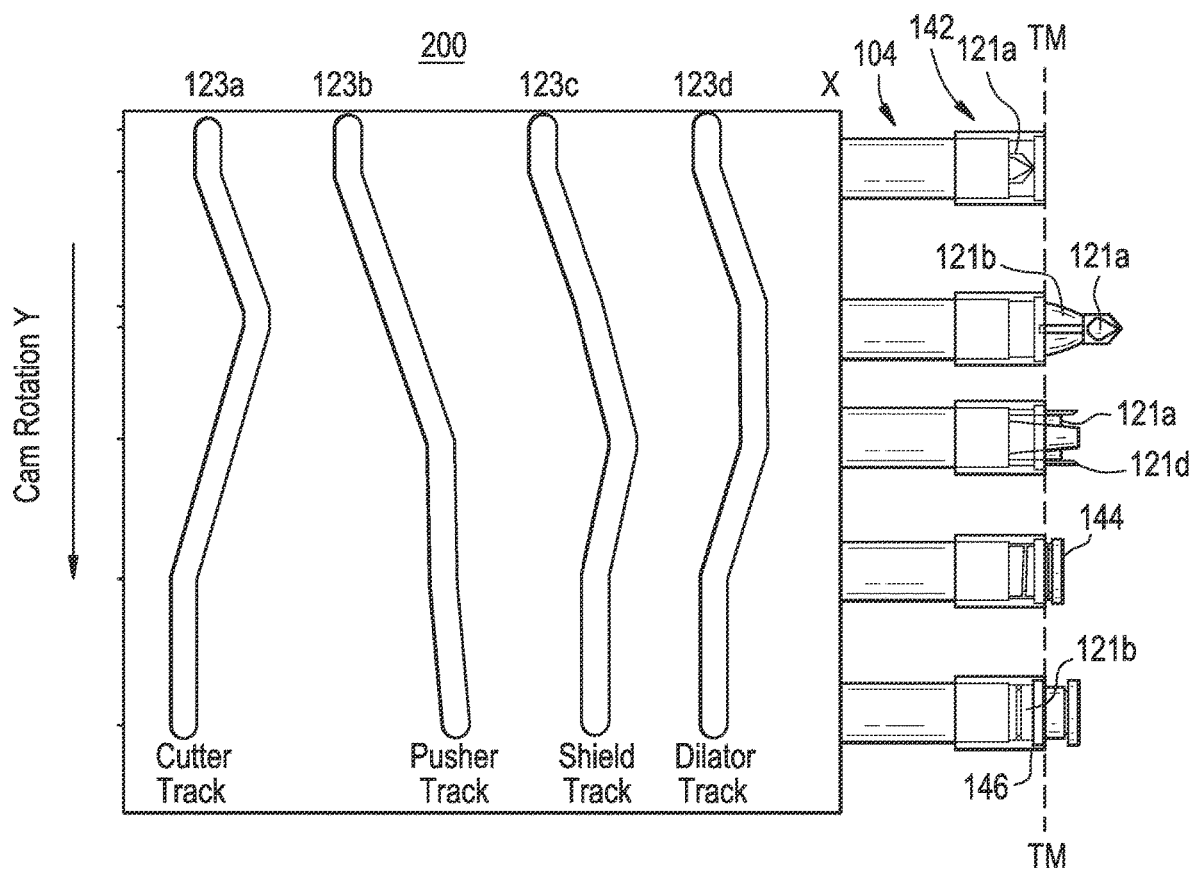
FIG. 2A is a displacement and operational diagram, according to one embodiment of the invention.

Methods of Operating of the Exemplary Delivery System:

FIG. 2A shows a displacement diagram 200 of the camshaft 112 and corresponding simplistic views of the distal tip of the shaft assembly 104 placed within an ear canal, with the tip 142 against a tympanic membrane TM. The displacement diagram 200 shows patterns of respective tracks 123a-d along axis X and Y. Axis Y represents the linear displacement of the tracks 123a-d along the circumference of the camshaft 112. Axis X represents the linear displacement of the tracks perpendicular axis Y.

As previously noted, the pins 122a-d follow movement of the tracks 123a-d. The pins 122a-d are attached to corresponding cam followers 120a-d. Thus, movement of the pins 122a-d results in movement of the corresponding cam followers 120a-d and respective movement of portions of the shaft assembly 104 along axis A-A, which is parallel to Axis X. Each track 123a-d is shown with a numeric displacement value at the various positions. The numeric displacement values are the distances in millimeters between the distal end of the tip 142 and the distal most position of the related shaft assembly 104 portions 121a-d. The views of the distal tip of the shaft assembly 104 show incremental positioning with respect to the displacement diagram, however, the movement of the shaft assembly 104 and camshaft 112 is one continuous movement. In various embodiments, the camshaft 112 may take between about 5 milliseconds and about 500 milliseconds to rotate from the initial position to a final position, after the button 106 has been pressed. In other words, it may take from about 5 to about 500 milliseconds from the time the button 106 is pressed until a pressure equalization tube 140 is deployed in a TM using the device 100. In some embodiments, this time period may be between about 30 milliseconds and about 250 milliseconds, with average times of between about 100 milliseconds and about 130 milliseconds. In other embodiments, the time period may be outside the ranges listed above.

1. Initial Camshaft Position:

At the initial position of the camshaft 112, the shaft assembly 104 is positioned as shown in FIG. 1P. At this position, the button 106 has not been pressed to release the wound spring 114. The shaft assembly 104 has been advanced into the ear canal such that the tip 142 abuts a portion of the tympanic membrane TM. At the initial camshaft position, the cutting member 121a is 0.25 mm behind (i.e., proximal) the extreme distal end of the tip 142; the pusher 121b is 7.04 mm behind the tip 142; the shield 121c is 4.09 mm behind the tip 142; and the dilator 121d is 1.68 mm behind the tip.

2. First Camshaft Position:

At a first camshaft position, the button 106 has been pressed to release the wound spring 114 which rotates the camshaft 112 from the initial camshaft position to the first camshaft position. Accordingly, as described herein, movement of the camshaft causes the cam followers 120a-d to move respective portions of the shaft assembly 104. At the first camshaft position the cutting member 121a punctures the tympanic membrane TM and the dilator 121d follows to dilate the puncture site to a larger diameter. The pusher 121b and shield 121c also advance, but remain behind the tip 142. At the first camshaft position the cutting member 121a is 2.79 mm ahead (i.e., distal) of the extreme distal end of the tip 142; the pusher 121b is 1.66 mm behind the tip 142; the shield 121c is 1.04 mm behind the tip 142; and the dilator 121d is 1.37 mm ahead of the tip 142.

3. Second Camshaft Position:

The camshaft 112 rotates from the first camshaft position to a second camshaft position. At the second camshaft position, the shield 121*c* advances past the tip 142 to open the folding tip 138 of the dilator 121*b* and further dilate the puncture site, and the cutting member 121*a* retracts behind the dilator 121*b*. The pusher 121*b* also advances, but remains behind the tip 142. At the second camshaft position the cutting member 121*a* is 0.58 mm ahead of the extreme distal end of the tip 142; the pusher 121*b* is 1.55 mm behind the tip 142; the shield 121*c* is 0.66 mm ahead of the tip 142; and the dilator 121*d* remains 1.37 mm ahead of the tip 142.

4. Third Camshaft Position:

The camshaft 112 rotates from the second camshaft position to a third camshaft position. At the third camshaft position, the cutting member 121*a* and dilator 121*d* retract behind the tip 142. The shield 121*c* also retracts, while the pusher 121*b* advances to partially push the tympanic membrane equalization tube 140 out of the shield 121*c*. A medial flange 144 (or "distal flange") of the tympanic membrane equalization tube 140 is pushed out of the shield 121*c* to expand medial (or "distal") to the tympanic membrane. At the third camshaft position the cutting member 121*a* is 1.78 mm behind the extreme distal end of the tip 142; the pusher 121*b* is 1.45 mm behind the tip 142; the shield 121*c* is 1.02 mm behind the tip 142; and the dilator 121*d* is 1.23 mm behind the tip 142.

5. Final Camshaft Position:

The camshaft 112 rotates from the third camshaft position to a final camshaft position. At the final camshaft position, the cutting member 121*a*, shield 121*c*, and dilator 121*d* remain stationary with respect to the third camshaft position. The pusher 121*b* advances to a final position, but remains behind the tip 142, to push a lateral flange 146 (or "proximal flange") of the tympanic membrane equalization tube 140 outside of the shield 121*c* to expand within the tip 142 of the device 100 and lateral (or "proximal") to the tympanic membrane. At the final camshaft position the cutting member 121*a* is 1.78 mm behind the extreme distal end of the tip 142; the pusher 121*b* is 0.84 mm behind the tip 142; the shield 121*c* is 1.02 mm behind the tip 142; and the dilator 121*d* is 1.23 mm behind the tip 142.

Figure 2B:
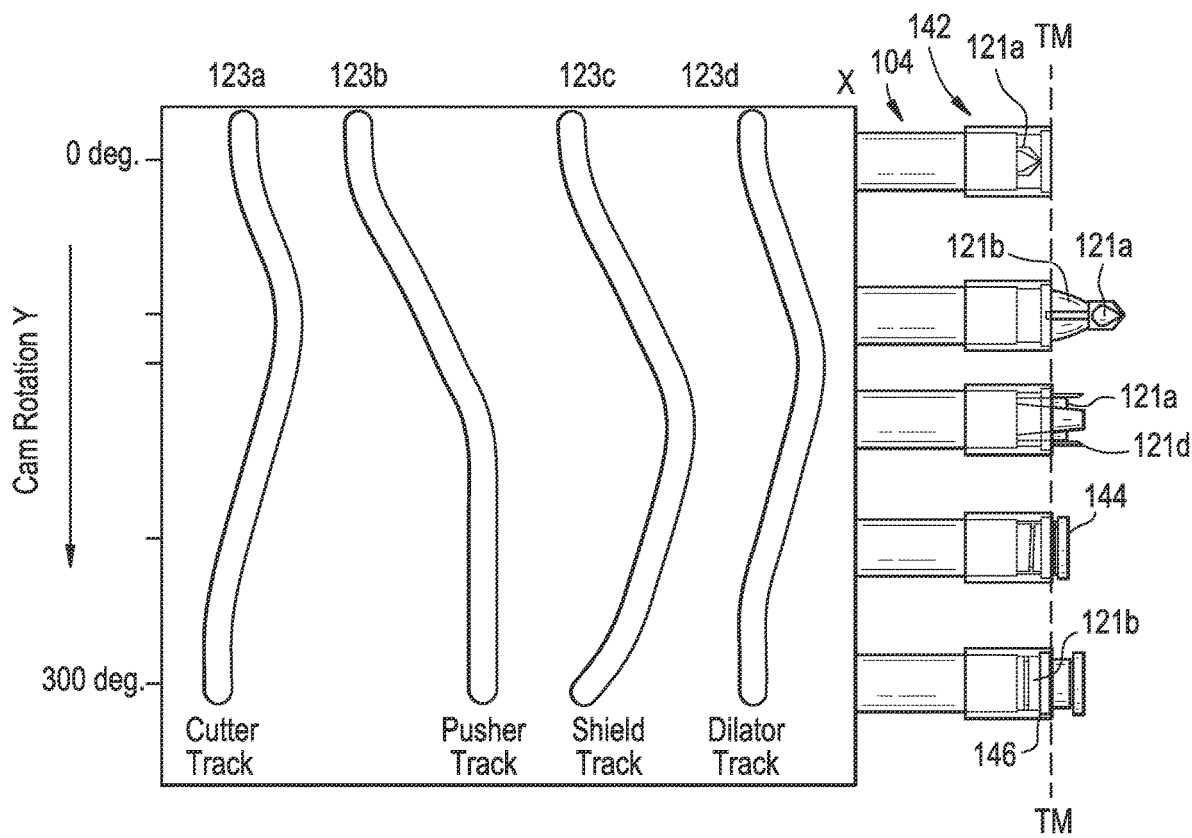
FIG. 2B is a displacement and operational diagram, according to one embodiment of the invention.

An alternative embodiment for the camshaft design is depicted in FIG. 2B. Reference to the above description of the various camshaft positions are applicable to this embodiment with the exception of slightly modified advancement points along the tracks of the cam as noted in the figure. The most noticeable variation is that shield 123*c* retracts further back into the shaft in the final camshaft position relative to the camshaft depiction of FIG. 2A.

When the pressure equalization tube 140 has been successfully placed, with the medial flange 144 and lateral flange 146 flanking the TM, the shaft assembly 104 may then be withdrawn from the ear canal, leaving the tube 140 behind. The above steps may then be repeated, if desired, in the patient's other ear using a second device 100 or by reloading the first device 100 with another equalization tube 140. In some embodiments, device 100 may be reloadable, while in alternative embodiments device 100 may be a one-use device only. Thus, according to the method described above, by simply positioning the delivery system 100 within the ear canal, with the tip 142 against the tympanic membrane TM, and pressing button 106, the delivery system 100 both punctures the tympanic membrane TM and also delivers the tympanic membrane equalization tube 140 in one effective movement.

Alternative Structure of the Delivery System:

Referring now to FIG. 3, in one alternative embodiment, a tympanic membrane pressure equalization tube delivery system 300 may include a pencil grip 302 handle and a trigger 304 for activating the delivery system 300. The delivery system 300 may be configured similarly to the delivery system 100, and may include a substantially similar internal tympanic membrane equalization tube delivery mechanism and shaft assembly. However, the delivery system 300 features the pencil grip 302 which may be ergonomically similar to grips of standard myringotomy spears. The trigger 304 may be placed in any convenient ergonomic location, such as on the top of the system 300, as shown. In other alternative embodiments, other handle and/or trigger configurations may be used including the configuration depicted in FIGS. 1E through 1G.

With reference now to FIGS. 4A-4D, in two alternative embodiments, a TM tube delivery device may include a cutting dilator 400 at its distal end, rather than including a separate cutter and dilator. In other words, the cutting dilator 400 integrates the cutting member 121*a* and dilator 121*d*. The cutting dilator 400 is capable of puncturing a tympanic membrane and also expanding to dilate a puncture site. The cutting dilator 400 includes a plurality of fingers 402 arranged as a cone. In the examples shown, four fingers 402 are used. More fingers 402 generally allow easier expansion. At least one of the fingers 402 includes a sharpened tip (FIGS. 4A and 4B) or cutting blade (FIGS. 4C and 4D) for puncturing the tympanic membrane. The cutting dilator 400 may be made from any suitable material that can be expanded from a closed to a dilated configuration. For example, in one embodiment, the dilator 400 may be formed from a super-elastic nickel-titanium alloy. In another embodiment, the cutting dilator 400 may be formed from a malleable material, such that when the cutting dilator 400 dilates it retains approximately the dilated configuration.

FIG. 4E shows, in one alternative embodiment, an alternate construction, and method for use, for the distal end of the shaft assembly 404. The shaft assembly 404 is constructed similarly to the shaft assembly 104 shown in FIG. 1E. However, outer shaft 406 includes an outer wall 408 and an inner wall 410, with a space 412 therebetween. The space 412 can be fluidly connected to a negative air pressure source, which is connected to the housing 102. The housing 102 can include an additional trigger device for enabling negative pressure to be applied to the space 412. Negative pressure may also be enabled and/or disabled by an automatic process, for example by port/valve triggered by the rotation of the camshaft 112. The outer shaft 406 can be a constructed, for example, from two individual tubes, from a double walled extrusion with a connecting member therebetween, or from a single walled extrusion including a plurality of lumens. The outer shaft 406 remains small enough in diameter, compared to the outer shaft 121*e*, to enable visualization and access through typical ear canal, and also reach any quadrant of TM. The outer shaft 406 can provide a suction force to the tympanic membrane TM in order to elevate a portion of the tympanic membrane TM away from a normal position.

Elevating the tympanic membrane can result in reduction of noise admittance during penetration of the cutting member 136. Elevating the tympanic membrane can also provide local stabilization of a target site to enhance the reliability of use of the system 100, thus preventing accidental deviation or slipping of the cutting member 136 during penetration. Elevation of tissue, can also be especially useful for patients with retraction pockets. Long term retraction of the eardrum, caused by negative pressure in the middle ear, will cause erosion of the ear canal and formation of a deep pocket. Eventually the pocket may trap skin, forming a skin cyst or cholesteatoma. Further progression of retraction pockets can cause destruction of the tympanic membrane. Tissue elevation enhances safety by providing additional space away from anatomical structures distal to the tympanic membrane for penetration and placement of the tympanic membrane pressure equalization tube 140. Accordingly, tissue elevation also allows a larger patient population to be treated, as a significant portion of patients who require placement of tympanostomy tubes have some degree of retraction.

In use, with reference to FIGS. 2A/2B and 4E, negative pressure may be applied to the space 412 of the outer shaft 406, before pressing button 106. The distal end of the outer shaft 406 may brought into contact, or near contact, with the tympanic membrane TM before, or after applying negative pressure. The negative pressure causes the tympanic membrane TM to temporarily attach to the distal end of the outer shaft 406. The tympanic membrane TM may then be elevated by pulling or placing the distal end of the outer shaft 406 in a proximal position (i.e., towards the outer ear) from the current position of the tympanic membrane TM. Tissue elevation is illustrated by movement of the dotted lines to solid lines, which represent the tympanic membrane TM in pre- and post-elevation positions, respectively. Thus, after elevation, additional space is provided away from anatomical structures distal to the tympanic membrane TM, for penetration and placement of the tympanic membrane pressure equalization tube 140. After the tympanic membrane TM has been elevated to a desired position, the button 106 may be pressed to initiate automatic placement of the tympanic membrane pressure equalization tube 140 in the tympanic membrane TM, while negative pressure is continually applied to the tympanic membrane TM. After the tympanic membrane pressure equalization tube 140 is placed, application of negative pressure to the space 412 of the outer shaft 406 can be stopped, thus releasing the tympanic membrane TM from the outer shaft 406. Alternatively, application of negative pressure to the space 412 of the outer shaft 406 can be stopped at other points of the method shown in FIGS. 2A/2B, for example after the medial flange 144 of the tympanic membrane equalization tube 140 is pushed out of the shield 121c to expand medial to the tympanic membrane.

Figure 4C:
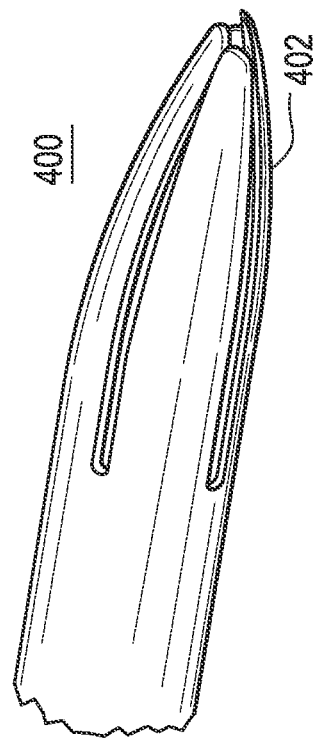
FIGS. 4A through 4D are perspective and side views of an integrated cutting member and dilator, according to two embodiments of the invention.
Figure 4D:
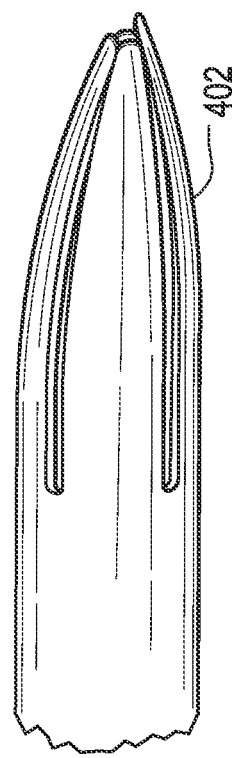
Figure 4A:
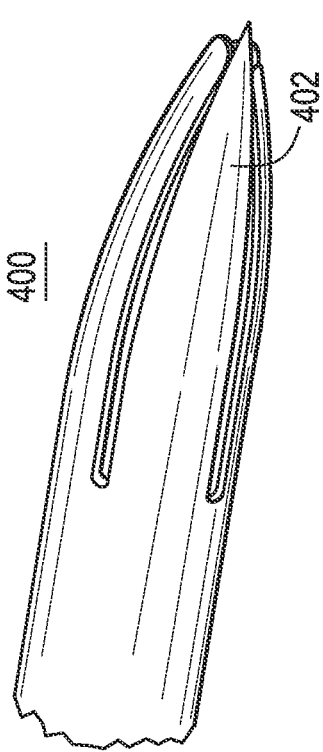
Figure 4B:
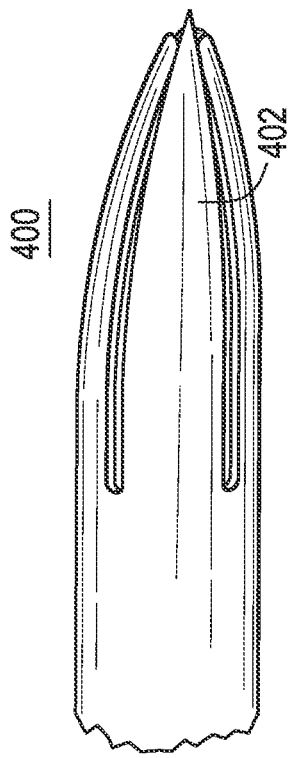
Figure 4F:
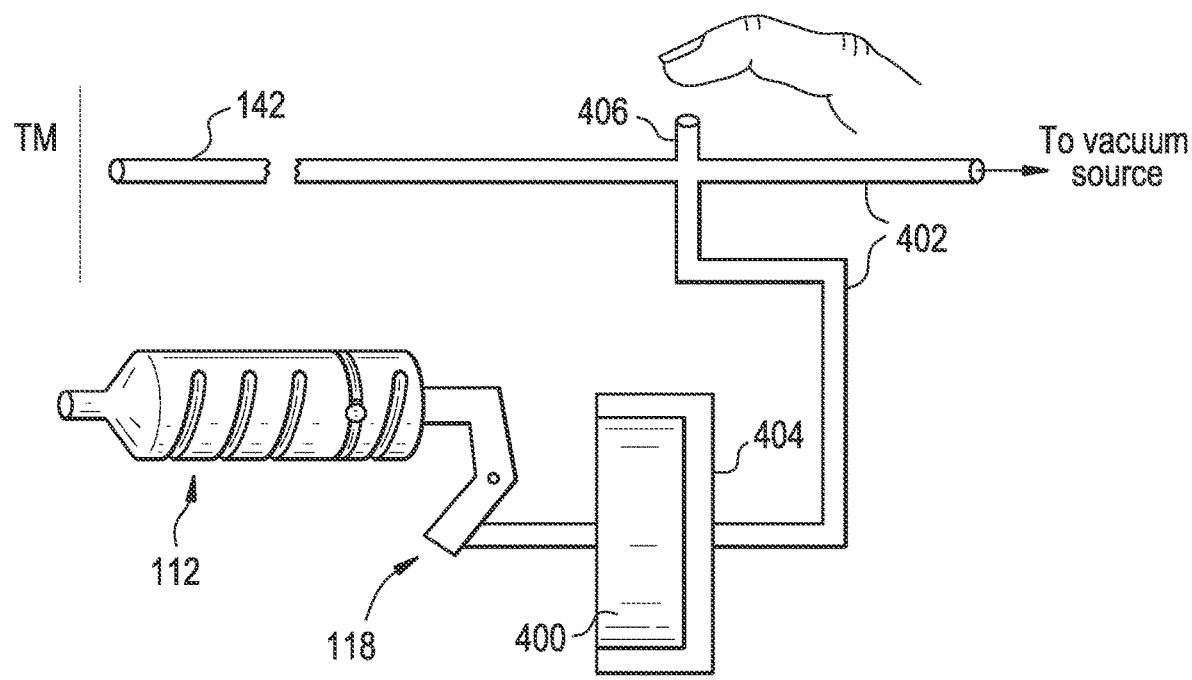
FIG. 4F depicts a schematic of a negative pressure actuation system, according to one embodiment of the invention.

An addition to the above alternate embodiment would include using the applied negative pressure as a means to actuate the device. FIG. 4F depicts a schematic of a potential negative pressure actuation system. A piston or bellows 400 within the delivery system 100 connected to the link 118 could move upon exposure to negative pressure and trigger the camshaft 112 rotation. The negative pressure on the piston or bellows could be generated when the tip 142 of the device attains apposition against the tympanic membrane thus ensuring the device position relative to the tympanic membrane.

The system includes a vacuum chamber 402 that has a contiguous, sealed lumen providing communication between the device tip 142 (that comes into contact with the tympanic membrane) and the proximal end of the delivery system 100. The chamber includes a vacuum actuated trigger mechanism such as vacuum cylinder 404 and piston 400 and a vacuum port 406 that can be attached to a vacuum source such as through a vacuum line normally available in an operating room or other clinical setting.

Advantages of the above embodiment include more accurate and consistent PE tube deployment into the tympanic membrane, minimal button actuation force providing greater device stability, and ensuring delivery system actuation when the device tip is fully opposed to the tympanic membrane.

Other mechanisms or structure may be employed in lieu of, or in conjunction with, application of negative pressure to the tympanic membrane, for elevation thereof For example, an adhesive or sticky substance may be used, or a mechanical application using micro-barbs.

Figure 5A:
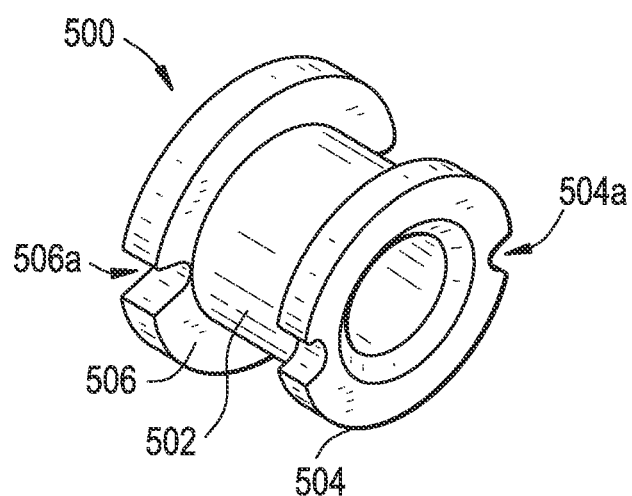
FIGS. 5A and 5B are perspective and side views, respectively, of a tympanic membrane equalization tube, according to one embodiment of the invention.
Figure 5B:
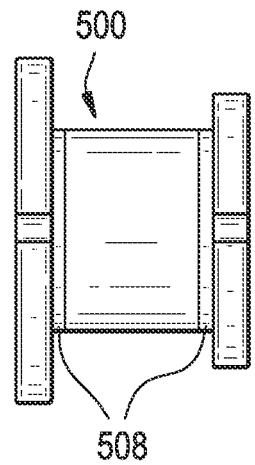

Tympanic Membrane Pressure Equalization Tube:

FIGS. 5A and 5B show a tympanic membrane pressure equalization tube 500, according to one embodiment of the invention. In this embodiment, the tube 500 is configured as a grommet made of silicone or some other pliable elastomeric material and is intended to be placed within a tympanic membrane to vent to the middle ear. Although a number of suitable pressure equalization tubes 500 may be used in conjunction with a delivery system as described above, in one embodiment the tube 500 may have an axial length of between about 2.0 mm and about 2.5 mm and ideally about 2.3 mm. The tube 500 may have an inner diameter of about 1.1 mm.

Figure 5C:
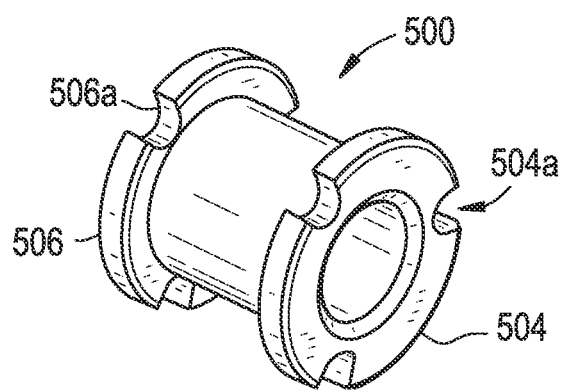
FIG. 5C is a perspective view of a tympanic membrane equalization tube, according to one embodiment of the invention.

A central lumen 502 of the tube 500 is flanked by an integral medial flange 504 and lateral flange 506. The medial flange 504 and lateral flange 506 prevent the tube 500 from falling out of an opening created in the tympanic membrane. In some embodiments, the lateral flange 504 can be smaller in diameter than the medial flange 506, as shown, as the lateral flange 504 can be expanded within the tip 142 of the delivery system 100, while the medial flange is intended to expand distally past the tympanic membrane. In alternative embodiments, the lateral flange 504 and medial flange 506 are of equal diameters. The exterior surface of the tympanic membrane equalization tube 500 includes optional flexible zones 508 which facilitate straightening of the medial flange 504 and lateral flange 506 for loading into a delivery system, as shown in FIG. 1P. The medial flange 504 and lateral flange 506 may also include optional notches or cutouts 504a, 506a which may further facilitate straightening of the flanges 504, 506. FIG. 5C, depicts one such further embodiment containing 3 notches or cutouts 504a and 506a on each of the flanges 504, 506. Alternative embodiments may of course contain any combination of these optional notches or cutouts 504a and 506a on the flanges, including having more notches on one flange compared with the other flange and also including optional flexible zones 508.

FIGS. 5D-5G show tympanic membrane pressure equalization tubes, according to other alternative embodiments of the invention. In some instances, the flanges of the tube, when constrained within a delivery system in a straightened position for a long period of time as shown in FIG. 1P, may not spring back (i.e., expand into) their unconstrained, natural position quickly enough for effective delivery into the TM. Therefore, in some embodiments, internal scaffolding may be included within the wall of the tube 510, 514, 518, 520 to help it reassume its natural shape. Such scaffolding may be constructed, for example, from a superelastic or shape-memory material, such as a nickel-titanium alloy, other metals, or polymers or other suitable materials. Also any of these embodiments may include the optional flexible zones 508 described above.

FIG. 5D shows a tympanic membrane pressure equalization tube 510 including an internal wire 512. The wire 512 provides a fast shape recovery for the tube 510. FIG. 5E shows a tube 514 including an internal double loop 516. The double loop 516 provides fast shape recovery for the tube 514, especially for the flanges. FIG. 5F shows a tube 518 including a plurality of wires 520. Using a plurality of wires 520 ensures uniform shape recovery of the tube 518. FIG.

5G shows a tube 520 including internal stent scaffolding 522, which promotes uniform shape recovery of the tube 520.

In many embodiments, the tympanic membrane equalization tubes disclosed herein can include features which help recover a misplaced tympanic membrane equalization tube. A misplaced tympanic membrane equalization tube located distally to the tympanic membrane can be especially difficult to remove. Such features can include tethers attached to any portion of the tympanic membrane equalization tubes. The tethers can be grasped proximally to the tympanic membrane and used to pull the misplaced tympanic membrane equalization tube out of the ear.

The present invention may be embodied in other specific forms without departing from the essential characteristics thereof These other embodiments are intended to be included within the scope of the present invention, which is set forth in the following claims.

What is claimed is:

1. A method, comprising:
    positioning a shaft assembly proximate to a tympanic membrane, the shaft assembly including: (i) a piercing element configured to form an incision in the tympanic membrane, and (ii) a shaft including an expandable feature;
    triggering, after positioning the shaft assembly proximate to the tympanic membrane, an actuation assembly including a cam such that the cam moves to advance a portion of the shaft assembly toward the tympanic membrane;
    forming, in response to advancing the portion of the shaft assembly, the incision in the tympanic membrane using the piercing element; and
    expanding the expandable feature of the shaft to dilate the incision.

2. The method of claim 1, wherein the portion of the shaft assembly is a first portion of the shaft assembly, the method further comprising:
    advancing a second portion of the shaft assembly toward the tympanic membrane relative to the first portion of the shaft assembly;
    deploying, in response to advancing the second portion of the shaft assembly, a tympanostomy tube in the incision in the tympanic membrane.

3. The method of claim 2, wherein the tympanostomy tube is configured to transition from a first state to a second state in which a first retention feature and a second retention feature of the tympanostomy tube are configured to maintain the tympanostomy tube in the tympanic membrane, and
    the deploying the tympanostomy tube includes pushing the tympanostomy tube into the incision and causing the tympanostomy tube to transition from the first state to the second state.

4. The method of claim 1, wherein the shaft includes the piercing element, and the advancing the portion of the shaft assembly includes advancing the shaft.

5. The method of claim 1, wherein the cam rotates to advance the portion of the shaft assembly toward the tympanic membrane.

6. The method of claim 1, wherein the shaft assembly includes a plurality of fingers disposed at the distal end of the shaft assembly, arranged as a cone and expandable from a closed configuration to a dilated configuration, the piercing element includes a sharpened tip of at least one of the fingers, the expandable feature includes the plurality of fingers, the forming the incision includes piercing the tympanic membrane with the sharpened tip, and the expanding includes expanding the plurality of flexible fingers from the closed configuration to the expanded configuration.

7. An apparatus, comprising:
    a body; and
    a shaft assembly extending distally from the body, the shaft assembly including a shaft including:
        a tubular portion defining a longitudinal axis; and
        an expandable portion including a plurality of fingers, at least one of the fingers of the plurality of fingers including a piercing element configured to form an incision in a tympanic membrane, each finger of the plurality of fingers configured to move outwardly relative to the longitudinal axis to transition the expandable portion from a first state to a second state to dilate the incision.

8. The apparatus of claim 7, wherein the expandable portion includes a plurality of fingers, each finger of the plurality of fingers configured to move outwardly relative to the longitudinal axis when the expandable portion transitions from the first state to the second state.

9. The apparatus of claim 8, wherein the plurality of fingers defines a conical structure when the expandable portion is in the first state.

10. The apparatus of claim 7, wherein the shaft is a first shaft, the shaft assembly including a second shaft disposed within the first shaft and configured to move relative to the first shaft along the longitudinal axis to cause the expandable portion to transition from the first state to the second state.

11. An apparatus, comprising:
    a body;
    a shaft assembly extending distally from the body and including a plurality of coaxially-arranged shafts;
    an actuation assembly configured to move the plurality of coaxially-arranged shafts to deploy a tympanostomy tube in a tympanic membrane; and
    a trigger assembly including:
        a link configured to pivot between a first position in which the link is engaged with the actuation assembly and prevents movement of the actuation assembly and a second position in which the link is disengaged from the actuation assembly and enables movement of the actuation assembly; and
        a release mechanism configured to pivot the link from the first position to the second position.

12. The apparatus of claim 11, wherein the actuation assembly includes:
    a cam configured to rotate to move the plurality of coaxially-arranged shafts; and
    a spring coupled to the cam and configured to transition from a loaded state to a released state to rotate the cam.

13. The apparatus of claim 12, wherein the spring is configured to transition from the loaded state to the released state when the link is in the second position.

14. The apparatus of claim 11, wherein the release mechanism includes a button movable to pivot the link in response to a pressure applied by a user.

15. The apparatus of claim 11, further comprising a dampening mechanism configured to reduce energy generated within the apparatus.

16. A method, comprising:
    positioning a shaft assembly proximate to a tympanic membrane, the shaft assembly including: (i) a plurality of fingers disposed at the distal end of the shaft assembly arranged as a cone and expandable from a closed configuration to a dilated configuration, (ii) a piercing element including a sharpened tip of at least one of the fingers configured to form an incision in the tympanic membrane;

advancing a portion of the shaft assembly toward the tympanic membrane;

forming, in response to advancing the portion of the shaft assembly, the incision in the tympanic membrane using the piercing element to pierce the tympanic membrane with the sharpened tip; and expanding the plurality of flexible fingers from the closed configuration to the expanded configuration to dilate the incision.

* * * * *